United States Patent
Thomson et al.

(10) Patent No.: US 9,668,463 B2
(45) Date of Patent: Jun. 6, 2017

(54) MOUSE MODEL FOR ENGRAFTMENT POTENTIAL

(71) Applicant: Cellular Dynamics International, Inc., Madison, WI (US)

(72) Inventors: James Thomson, Madison, WI (US); Brian McIntosh, Verona, WI (US); Igor Slukvin, Madison, WI (US)

(*) Notice: Subject to any disclaimer, the term of this patent is extended or adjusted under 35 U.S.C. 154(b) by 0 days.

(21) Appl. No.: 15/026,856

(22) PCT Filed: Oct. 2, 2014

(86) PCT No.: PCT/US2014/058741
§ 371 (c)(1),
(2) Date: Apr. 1, 2016

(87) PCT Pub. No.: WO2015/051069
PCT Pub. Date: Apr. 9, 2015

(65) Prior Publication Data
US 2016/0219843 A1 Aug. 4, 2016

Related U.S. Application Data

(60) Provisional application No. 61/885,810, filed on Oct. 2, 2013.

(51) Int. Cl.
A01K 67/00 (2006.01)
A01K 67/027 (2006.01)

(52) U.S. Cl.
CPC ........ *A01K 67/0271* (2013.01); *A01K 67/027* (2013.01); *A01K 2207/12* (2013.01); *A01K 2207/15* (2013.01); *A01K 2217/075* (2013.01); *A01K 2227/105* (2013.01); *A01K 2267/03* (2013.01)

(58) Field of Classification Search
CPC .......................... A01K 67/0271; A01K 67/027
See application file for complete search history.

(56) References Cited

FOREIGN PATENT DOCUMENTS

DE    10 2012 207 453    11/2013

OTHER PUBLICATIONS

Quong et al. PLos ONE 4(8):e6679. pp. 1-10, 2009.*
Dolatshad et al. Mamm Genome 26:598-608, 2015.*
Bosma et al., "The mouse mutation severe combined immunodeficiency (scid) is on chromosome 16," *Immunogenetics*, 29:54-57, 1989.
Brehm et al., "Engraftment of human HSCs in nonirradiated newborn NOD-*scid* IL2rγ$^{null}$ mice is enhanced by transgenic expression of membrane-bound human SCF," *Blood*, 119(12):2778-2788, 2012.
Brehm et al., "Parameters for establishing humanized mouse models to study human immunity: analysis of human hematopoietic stem cell engraftment in three immunodeficient strains of mice bearing the IL2rγ$^{null}$ mutation," *Clinical Immunology*, 135(1):84-98, 2010.
Bueno et al., "Intra-bone marrow transplantation of human CD34$^+$cells into NOD/LtSz-*scid* IL-rγ$^{null}$ mice permits multilineage engraftment without previous irradiation," *Cytotherapy*, 12(1):45-49, 2010.
Cosgun et al., "Kit regulates HSC engraftment across the human-mouse species barrier," *Cell Stem Cell*, 15(2):227-238, 2014.
Geissler et al., "Analysis of pleiotropism at the dominant white-spotting (*W*) locus of the house mouse: a description of ten new *W* alleles," *Genetics*, 97(2):337-361, 1981.
Hayakawa et al., "Busulfan produces efficient human cell engraftment in NOD/LtSz-*scid* IL2Rγ$^{null}$ mice," *Stem Cells*, 27(1):175-182, 2009.
Ishikawa et al., "Development of functional human blood and immune systems in NOD/SCID/IL2 receptor γ chain$^{null}$ mice," *Blood*, 106:1565-1573, 2005.
Ito et al., "NOD/SCID/γ$_c^{null}$ mouse: an excellent recipient mouse model for engraftment of human cells," *Blood*, 100:3175-3182, 2002.
JAX Mice Database, "Strain Name: C57BL/6J-*Kit*$^{W-41J}$/J," 2011.
JAX Mice Database, "Strain Name: NOD.Cg-*Prkdc*$^{scid}$ *Il2rg*$^{tm1Wjl}$/SzJ," 2013.
McIntosh et al., "Nonirradiated NOD,B6.SCID Il2rγ$^{-/-}$-Kit$^{W41/W41}$ (NBSGW) mice support multilineage engraftment of human hematopoietic cells," *Stem Cell Reports*, 4:171-180, 2015.
Nocka et al., "Molecular bases of dominant negative and loss of function mutations at the murine *c-kit*/white spotting locus: $W^{37}$, $w^v$, $W^{41}$ and $W$," *The EMBO Journal*, 9(6):1805-1813, 1990.
Ohbo et al., "Modulation of hematopoiesis in mice with a truncated mutant of the interleukin-2 receptor gamma chain," *Blood*, 87(3):956-967, 1996.
PCT International Preliminary Report on Patentability issued in International Application No. PCT/US2014/058741, mailed Apr. 14, 2016.
PCT International Search Report and Written Opinion issued in International Application No. PCT/US2014/058741, mailed Feb. 3, 2015.
Reith et al., "W mutant mice with mild or severe developmental defects contain distinct point mutations in the kinase domain of the c-kit receptor," *Genes & Development*, 4(3):390-400, 1990.
Schultz et al., "Human lymphoid and myeloid cell development in NOD/LtSz-*scid*IL2Rγ$^{null}$ mice engrafted with mobilized human hematopoietic stem cells," *The Journal of Immunology*, 174(10):6477-6489, 2005.
Schultz et al., "Humanized mice in translational biomedical research," *The Journal of Immunology*, 7(2):118-130, 2007.
Traggiai et al., "Development of a Human Adaptive Immune System in Cord Blood Cell-Transplanted Mice," *Science*, 304:104-107, 2004.
Waskow et al., "Hematopoietic stem cell transplantation without irradiation," *Nature Methods*, 6(4):267-269, 2009.
Waskow et al., "Stable human hematopoietic stem cell engraftment supports continuous de novo generation of mature human blood cells in mice," *Experimental Hematology*, 41(8):S11, 2013.

* cited by examiner

*Primary Examiner* — Marcia S Noble
(74) *Attorney, Agent, or Firm* — Parker Highlander PLLC

(57) ABSTRACT

Disclosed herein is the generation of a permissive murine strain (NSGW) that exhibits enhanced levels of human chimerism without pre-conditioning.

17 Claims, 12 Drawing Sheets

```
C57BL/6J  ATCTTTCTTCCCAGGAGCCACGGGGAAGGAACTGAAGGTGACT
NOD       ATTTTTCTTCCCAGGAGCCACGAGGACAGAAGTGAAGGTGATT
```

MOUSE MODEL FOR ENGRAFTMENT POTENTIAL

The present application is a national phase application under 35 U.S.C. 371 of International Application No. PCT/US2014/058741, filed Oct. 2, 2014, which claims the priority benefit of U.S. provisional application No. 61/885,810, filed Oct. 2, 2013, the entire contents of each of which is incorporated herein by reference.

The invention was made with government support under Grant No. U01HL099773 awarded by the National Institutes of Health. The government has certain rights in the invention.

BACKGROUND OF THE INVENTION

1. Field of the Invention

The present invention relates generally to the field of biology. More particularly, it concerns transplantation and engraftment of xenogeneic hematopoietic stem cells without pre-conditioning.

2. Description of Related Art

Engrafting human hematopoietic stem cells (HSC) requires pre-conditioning immunodeficient recipients (e.g., mice) with a sub-lethal to lethal dose of total body irradiation (TBI). Such TBI pre-conditioning is shown to increase proliferation of HSCs through the expression of survival factors required for positive HSC engraftment. However, the side effects of TBI can include skeletal alterations, pneumonitis, proctitis, enteritis, colitis, esophagitis, dermatitis, and cerebellar damage. Unless death occurs, these side effects, which decrease the overall health of the recipient, often go unnoticed. Therefore, experimental engraftment results may be adversely reported when TBI is used.

SUMMARY OF THE INVENTION

In one embodiment of the invention, a mouse is provided whose genome comprises (i) a homozygous non-obese diabetic (NOD) polymorphism of a Sirpa gene; (ii) a homozygous scid mutation of a Prkdc gene; (iii) a homozygous disruption of a Il2rγ gene; and (iv) a homozygous W41 mutation of a Kit gene.

In one aspect, the mouse may comprise a homozygous G/G genotype at nucleotide 291 in a Tyrosinase gene. In this aspect, the mouse is not albino.

In some aspects, the mouse may be immunodeficient. In certain aspects, the mouse may have a C57BL/6J genetic background.

In one aspect, the homozygous scid mutation of the Prkdc gene may be a T to A transversion at codon 4095, which creates a premature stop codon. In one aspect, the homozygous disruption of the Il2rγ gene may be a homozygous replacement of part of exon 3 and all of exons 4-8 of the Il2rγ gene with a neomycin resistance cassette. In one aspect, the homozygous W41 mutation of the Kit gene may be a homozygous V831M mutation. One example of a mouse of the present embodiment is a NOD.Cg-Prkdc$^{scid}$Il2rg$^{tm1Wjl}$/SzJ mouse whose genome comprises a Kit V831M mutation.

In certain aspects, a mouse of the present embodiment may comprise xenogeneic hematopoietic stem cells (e.g., human hematopoietic stem cells). The hematopoietic stem cells may be CD34+ umbilical cord blood-derived cells.

In one embodiment, a method is provided for xenogeneic stem cell engraftment in a mouse of the embodiments. The method comprises administering xenogeneic stem cells to the mouse in the absence of conditioning of the mouse. As such, the mouse is not irradiated prior to administering the xenogeneic stem cells. In one aspect, the mouse may be an immune-system humanized mouse.

In certain aspects, the xenogeneic stem cells may be xenogeneic hematopoietic stem cells (e.g., human hematopoietic stem cells). The hematopoietic stem cells may be CD34+ umbilical cord blood-derived cells.

In some aspects, the engraftment level of the xenogeneic hematopoietic stem cells into the bone marrow or spleen of the recipient mouse may be measured. In one aspect, the engraftment level of the xenogeneic hematopoietic stem cells (e.g., human CD45+ cells) in the bone marrow of the recipient mouse may be 80% or more. In a further aspect, the level may be 90% or more. In another aspect, the engraftment level of xenogeneic hematopoietic stem (e.g., human CD45+ cells) in the spleen of the recipient mouse may be 80% or more. In a further aspect, the level may be 90% or more.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7—A portion of the sequence of the murine Sirpa allele from C57BL/6J (SEQ ID NO: 12) and NOD (SEQ ID NO: 13) strains. The underlined characters illustrate the NOD polymorphisms.

DESCRIPTION OF ILLUSTRATIVE EMBODIMENTS

Figure 1:
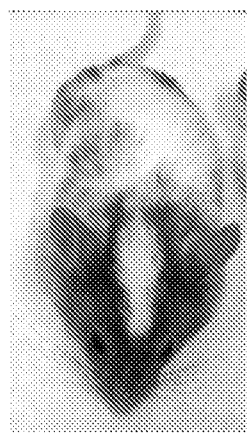
FIG. 1—NOD.B6-Prkdc$^{scid}$ Il2rg$^{tm1Wjl/SzJ}$ Kit$^{W41/W41}$ (NSGW) mouse.

Current mouse engraftment models require some form of immunosuppression (irradiation) to engraft human HSCs at similar levels as the inventors' NSGW strain without irradiation. Further, the engraftment kinetics of the inventors' NSGW model versus the commonly used NSG model indicates its increased engraftment sensitivity.

Using two conventional mouse strains, the immunocompromised standard of the field, NSG, and a strain possessing a defective Kit allele (c-Kit, $W^{41}$), the inventors generated a mouse strain (NSGW$^{41}$) that does not require total body irradiation to successfully engraft human hematopoietic stem cells (HSCs). To do this, the inventors crossed mice harboring the Kit$^{W41}$ mutation with the NSG strain, bred to homozygosity for Prkdc$^{scid}$, Il2r$\gamma^{-/-}$, Kit$^{W41}$, and selected for those animals that maintained the NOD Sirpa allele.

Following the transplantation of human cord blood CD34+ HSCs into non-irradiated adults of both NSG and NSGW$^{41}$ strains, detectable levels of human CD45+ cell chimerism were observed. The chimerism was two- to eight-fold greater in the NSGW$^{41}$ strain over a time course when compared to the standard NSG strain. In short, the inventors generated a mouse model that is superior in engraftment potential to the commonly used strain and which does not require irradiation.

Two previous studies have demonstrated the ability of the NSG strain to engraft human cells without irradiation (Bueno et al., 2010; Brehm et al., 2012). The first study transplanted 1.5×10$^5$ CD34+ CBCs into the femur. This study reports an average of 3% (range 0.5%-8%) of the cells to express huCD45 in the peripheral blood after 10 weeks (Bueno et al., 2010). Interestingly, this study reports that 5% of the spleen and 13% of both femurs to be huCD45+. However, each measurement is accompanied by a large variance.

The second study xenografted 3×10$^4$ CD34+ CBCs into non-myeloablated newborn NSG hosts via intracardiac injection. Twelve-weeks post injection 18.3%±13% of the peripheral blood was αhuCD45+ (Brehm et al., 2012). Of note, this study also discussed the generation of a novel murine strain transgenically expressing SCF. The human cell chimerism in was reported at 12.5%±6.5%. Further, it was reported that both strains exhibit extended chimerism in the spleen and marrow, again accompanied by a large range for both.

In line with the two previous reports, the inventors' data concerning the xenograft level in the nonirradiated NSG mice agrees (Bueno et al., 2010; Brehm et al., 2012). Given the differing ages of the animals, the routes of injection and the number of cells may also indicate that the maximum space for engraftment in the NSG mouse was reached. However, the NSGW strain was 9-fold higher (average 65% vs. 8.3% when compared to NSG) in human chimerism in the peripheral blood. This is the highest report to date of human cell engraftment, accompanied with the least variance, in a murine organism without using irradiation.

Figure 3:
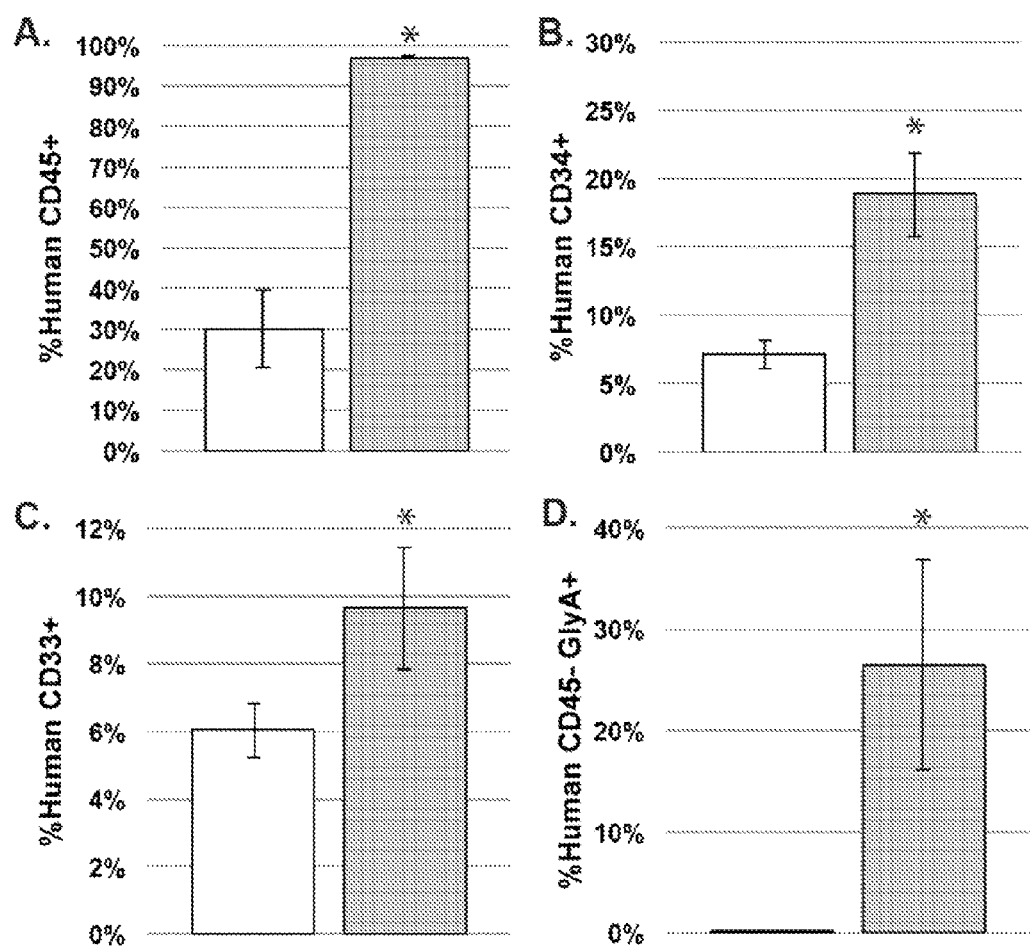
FIGS. 3A-D—Human chimerism and lineage development observed in the bone marrow of non-irradiated NSG (white) and NSGW (grey) mice at 12-weeks post engraftment. (A) The percentage of human CD45+ leukocytes. The percentage of human (B) CD34+ cells and (C) CD33+ cells observed in the human CD45+ fraction. (D) The percentage of human Glycophorin A+ cells observed. Error is represented by stdev (N=5, *p<0.01).

The inventors also observed a statistically significant increase in the human chimerism in bone marrow and spleen of the NSGW strain compared to the NSG strain. Further analyzing the human CD45+ population of the marrow indicates preferential engraftment and competition of human CD34+ cells and resident myeloid cells (CD33+, FIG. 3). In addition the inventors' observed a human erythroid population (CD45-Glycophorin A+) in the marrow, indicating the production of human erythrocytes (FIG. 3). These values observed in the NSGW strain are significantly higher than any value reported for the NSG or the NSG-(TgSCF) without irradiation (Brehm et al., 2012).

I. IMMUNODEFICIENT MICE

The term "severe combined immune deficiency (SCID)" refers to a condition characterized by absence of T cells and lack of B-cell function. Common forms of SCID include: X-linked SCID, which is characterized by gamma chain gene mutations in the IL2rg gene and the lymphocyte phenotype T(−) B(+) NK(−); autosomal recessive SCID characterized by Jak3 gene mutations and the lymphocyte phenotype T(−) B(+) NK(−); ADA gene mutations and the lymphocyte phenotype T(−) B(−) NK(−); IL-7R alpha-chain mutations and the lymphocyte phenotype T(−) B(+) NK(+); CD3 delta or epsilon mutations and the lymphocyte phenotype T(−) B(+) NK(+); RAG1/RAG2 mutations and the lymphocyte phenotype T(−) B(−) NK(+); Artemis gene mutations and the lymphocyte phenotype T(−) B(−) NK(+); and CD45 gene mutations and the lymphocyte phenotype T(−) B(+) NK(+). The scid mutation ($Prkdc^{scid}$) is well-known and located on mouse chromosome 16 as described in Bosma et al. (1989). Mice homozygous for the scid mutation are characterized by an absence of functional T cells and B cells, lymphopenia, hypoglobulinemia, and a normal hematopoetic microenvironment. The scid mutation can be detected, for example, by detection of markers for the scid mutation using well-known methods.

Backcrossing the C.B-17-scid mouse with the NOD/Shi mouse is done in accordance with methods well-known to a person skilled in the art, for example, backcrossing by Cross Intercross method (Inbred Strains in Biomedical Research, 1979). The C.B-17-scid mouse is crossed with the NOD/Shi mouse, and the obtained F1 mice are further crossed with each other. Then, the immunoglobulin amount in blood serum of the thus obtained F2 mice is measured for selecting a mouse, from which immunoglobulin cannot be detected. The selected mouse is again crossed with a NOD/Shi mouse. Repeating this process (Cross Intercross method) nine times or more enables the accomplishment of the backcrossing.

A NOD/Shi mouse and a C.B-17-scid mouse are both commercially available. Further, examples of mice obtained by crossing these mice with each other include a NOD/Shi-scid mouse (also called a NOD-scid mouse).

The term "IL2 receptor gamma chain deficiency" refers to decreased IL2 receptor gamma chain. Decreased IL2 receptor gamma chain can be due to gene deletion or mutation. Knockout of an interleukin 2-receptor γ-chain (IL2rg) gene can be carried out in accordance with methods well known to a person skilled in the art, for example, a homologous recombination method using mouse ES cells (Capecchi, 1989). After substituting a specific mouse-derived gene by a homologous gene including a gene resistant to a drug, for example neomycin etc. at ES cell stage, the ES cells are inserted into a fertilized egg, thereby accomplishing the gene-knockout. Decreased IL2 receptor gamma chain can be detected, for example, by detection of IL2 receptor gamma chain gene deletion or mutation and/or detection of decreased IL2 receptor gamma chain expression using well-known methods.

Specifically, for example, gene clones containing a mouse IL2rg are isolated, from a genome library of 129/SV mouse, using a human IL2rg cDNA as a probe. Using a fragment of 8.6 kb containing the full length of IL2rg among the clones, a targeting vector is prepared. That is, PMC1-neo poly A which expresses a neomycin resistant gene, is inserted between exons 7 and 8 of IL2rg in the fragment, and also a diphtheria toxin-A gene is placed at 3' side 1 kb away from exon 8. Next, the vector is made linear, and introduced into $1 \times 10^7$ of E14 ES cells by electroporation. Thereafter, ES clones which bring about homologous recombination in the culture solution including G418, are selected (confirmed by PCR or Southern method), and after injecting the ES clones into blastocysts of C57BL/6 mice, they are transplanted into the uteruses of foster parent mice. Chimeric mice born from the foster parent mice are further crossed with C57BL/6 mice, thereby obtaining IL2rgKO hetero mice wherein knockout is transduced to germ cells.

Pre-established interleukin-2 receptor γ chain gene (IL2rg) knockout mouse strain may directly be obtained for use from suppliers, and examples of the mouse strains include interleukin-2 receptor γ chain (IL2rg) knockout mice (Ohbo et al., 1996), which was produced from IL2rgKO mouse strains.

The terms "NOD scid gamma" and "NSG" are used interchangeably herein to refer to a well-known immunodeficient mouse strain NOD.Cg-$Prkdc^{scid}$ $Il2rg^{tm1Wjl}$/SzJ. NSG mice combine multiple immune deficits from the NOD/ShiLtJ background, the severe combined immune deficiency (scid) mutation, and a complete knockout of the interleukin-2 receptor gamma chain. As a result, NSG mice lack mature T, B and NK cells, and are deficient in cytokine signaling. NSG mice are characterized by lack of IL2rg (gamma c) expression, no detectable serum immunoglobulin, no hemolytic complement, no mature T lymphocytes, and no mature natural killer cells. NSG mice may be prepared by known methods (Shultz et al., 2005). For example, NSG mice may be generated by backcross matings of C57BL/6J-γnull mice with NOD-SCID mice nine times.

The Kit oncogene encodes a type I membrane proteins (c-Kit) belonging to the type III tyrosine kinase growth factor receptor family (Yarden and Ullrich, 1988). The dominant negative $Kit^{W41/W41}$ mutation affects primarily the kinase but not other aspects of the c-Kit receptor. Comparison of the coding sequence of this allele with normal c-kit indicated a G to A point mutation in the kinase domain at nucleotide 2519 that results in a valine to methionine substitution at amino acid 831.

II. HEMATOPOIETIC STEM CELLS AND TRANSPLANTATION THEREOF

A. Hematopoietic Stem Cells

"Hematopoietic stem cells" or "HSCs" are primitive cells capable of regenerating all blood cells. During development, the site of hematopoiesis translocates from the fetal liver to the bone marrow, which then remains the site of hematopoiesis throughout adulthood. HSCs as used herein refers to pluripotent stem cells or multipotent stem cells or lymphoid or myeloid (derived from bone marrow) stem cells that, upon exposure to an appropriate cytokine or plurality of cytokines, can either differentiate into a progenitor cell of a lymphoid, erythroid, or myeloid cell lineage or proliferate as a stem cell population without further differentiation being initiated. HSCs can be isolated from bone marrow, peripheral blood, umbilical cord blood, or embryonic stem cells. HSCs can form cells such as erythrocytes (e.g., reticulocytes, erythrocytes), thrombocytes (e.g., megakaryoblasts, platelet producing megakaryocytes, platelets), granulocytes (e.g., promyelocytes, neutrophils, eosinophils, basophils)), monocytes (e.g., monocytes, macrophages), and/or lymphocytes (e.g., B cells, T cells, natural killer cells). HSC are capable of self-renewal or remaining a stem cell after cell division. HSCs are also capable of differentiation or starting a path to becoming a mature hematopoietic cell. HSCs can also be regulated in their mobility or migration or can be regulated by apoptosis or programmed cell death.

The terms "progenitor" and "progenitor cell" as used herein refer to primitive hematopoietic cells that have differentiated to a developmental stage that, when the cells are further exposed to an appropriate cytokine or a group of cytokines, they will differentiate further along the hematopoietic cell lineage. In contrast to HSCs, progenitors are only capable of limited self-renewal and are not capable of long-term self-renewal. Thus, hematopoietic progenitor cells can restore and sustain hematopoiesis for three to four months (Marshak et al., 2001) and are important for recovery in the period immediately following a hematopoietic progenitor cell transplant in an individual.

"Progenitors" and "progenitor cells" as used herein also include "precursor" cells that are derived from differentiation of progenitor cells and are the immediate precursors of mature differentiated hematopoietic cells. The terms "progenitor" and "progenitor cell" as used herein include, but are not limited to, granulocyte-macrophage colony-forming cell (GM-CFC), megakaryocyte colony-forming cell (Mk-CFC), burst-forming unit erythroid (BFU-E), B-cell colony-forming cell (B-CFC), and T-cell colony-forming cell (T-CFC). "Precursor cells" include, but are not limited to, colony-forming unit-erythroid (CFU-E), granulocyte colony-forming cell (G-CFC), colony-forming cell-basophil (CFC-Bas), colony-forming cell-eosinophil (CFC-Eo), and macrophage colony-forming cell (M-CFC) cells.

It is known in the art that HSCs may or may not include CD34+ cells. CD34+ cells are immature cells that express the CD34 cell surface marker. CD34+ cells are believed to include a subpopulation of cells with the stem cell properties defined above. HSCs include pluripotent stem cells, multipotent stem cells (e.g., a lymphoid stem cell), and/or stem cells committed to specific hematopoietic lineages. The stem cells committed to specific hematopoietic lineages can be of T cell lineage, B cell lineage, dendritic cell lineage, Langerhans cell lineage and/or lymphoid tissue-specific macrophage cell lineage. In addition, HSCs also refer to long-term HSC (LT-HSC) and short-term HSC (ST-HSC). A long-term stem cell typically includes the long-term (more than three months) contribution to multilineage engraftment after transplantation. A short-term stem cell is typically anything that lasts shorter than three months, and/or that is not multilineage. LT-HSC and ST-HSC are distinguished, for example, based on their cell surface marker expression. LT-HSC are CD34−, SCA-1+, Thy1.1+/lo, C-kit+, lin−, CD135−, Slamf1/CD150+, whereas ST-HSC are CD34+, SCA-1+, Thy1.1+/lo, C-kit+, lin−, CD135−, Slamf1/CD150+, Mac-1 (CD11b)lo (*Handbook of Stem Cells*, 2004). In addition, ST-HSC are less quiescent (i.e., more active) and more proliferative than LT-HSC. LT-HSC have unlimited self renewal (i.e., they survive throughout adulthood), whereas ST-HSC have limited self renewal (i.e., they survive for only a limited period of time). Any of these HSCs can be used advantageously in any of the methods described herein.

B. Isolation of Hematopoietic Stem Cells

HSCs can be obtained from a variety of sources including, for example, bone marrow, peripheral blood, placental blood, and umbilical cord blood. Bone marrow can be obtained by puncturing bone with a needle and removing bone marrow cells with a syringe (herein called "bone marrow aspirate"). HSCs can be isolated from the bone marrow aspirate by using surface markers specific for HSCs.

HSCs can also be obtained from peripheral blood of a progenitor cell donor. Prior to harvest of the cells from peripheral blood, the donor can be treated with a cytokine, such as granulocyte-colony stimulating factor, to promote cell migration from the bone marrow to the blood compartment. Cells can be collected via an intravenous tube and filtered to isolate white blood cells for transplantation. The white blood cell population obtained (i.e., a mixture of stem cells, progenitors and white blood cells of various degrees of maturity) can be transplanted as a heterogeneous mixture or HSCs can further be isolated using cell surface markers known to those of skill in the art.

Sources for HSC expansion also include aorta-gonad-mesonephros (AGM) derived cells, embryonic stem cells (ESC) and induced pluripotent stem cells (iPSC). ESCs are well-known in the art, and can be obtained from commercial or academic sources (Thomson et al., 1998). iPSC are a type of pluripotent stem cell artificially derived from a non-pluripotent cell, typically an adult somatic cell, by inducing a "forced" expression of certain genes (Baker, 2007; Vogel and Holden, 2007). ESC, AGM, and iPSC can be derived from animal or human sources. The AGM stem cell is a cell that is born inside the aorta, and colonizes the fetal liver.

The HSCs are preferably obtained from human donors, however, non-human donors are also contemplated, including non-human primates, pigs, cows, horses, cats, and dogs. A purified population of HSCs may be obtained by utilizing various methods known by persons skilled in the art and described in U.S. Pat. No. 5,677,136 and U.S. Pat. Pub. No. 2006/0040389, which are incorporated by reference in their entirety.

Hematopoietic cell samples (e.g., cord blood, peripheral blood, bone marrow), as well as committed progenitor cells destined to become neutrophils, erythrocytes, platelets, etc., can be purified to isolate and obtain artificially high concentrations of HSCs by detecting expression of specific cell surface proteins or receptors, cell surface protein markers, or other markers. HSCs may be physically separated from other cells within a cellular preparation of hematopoietic tissue using any previously developed or as yet undeveloped technique whereby cells are directly or indirectly differentiated according to their expression or lack of expression of particular surface proteins. Common methods used to physically separate specific cells from within a heterogenous population of cells within a hematopoietic cell preparation include but are not limited to flow cytometry using a cytometer which may have varying degrees of complexity and or detection specifications, magnetic separation, using antibody or protein coated beads, affinity chromatography, or solid-support affinity separation where cells are retained on a substrate according to their expression or lack of expression of a specific protein or type of protein. Such separation techniques need not, but may, completely purify or nearly completely purify (e.g., 99.9% are perfectly separated) HSCs or populations enriched in HSCs.

The CD34+-enriched human stem cell fractions can be separated by a number of reported methods, including affinity columns or beads, magnetic beads or flow cytometry using antibodies directed to surface antigens, such as CD34. Further, physical separation methods such as counterflow elutriation can be used to enrich hematopoietic progenitors. The CD34+ progenitors are heterogeneous, and can be divided into several subpopulations characterized by the presence or absence of coexpression of different lineage associated cell surface associated molecules. The most immature progenitor cells do not express any known lineage-associated markers, such as HLA-DR or CD38, but they can express CD90 (thy-1). Other surface antigens such as CD33, CD38, CD41, CD71, HLA-DR or c-kit can also be used to selectively isolate hematopoietic progenitors. The separated cells can be incubated in selected medium in a culture flask, sterile bag or in hollow fibers. Various hematopoietic growth factors can be utilized in order to selectively expand cells. Representative factors that have been utilized for ex vivo expansion of bone marrow include c-kit ligand, IL-3, G-CSF, GM-CSF, IL-1, IL-6, IL-11, flt-3 ligand or combinations thereof. The proliferation of stem cells can be monitored by enumerating the number of stem cells and other cells by standard techniques (e.g., hemocytometer, CFU, LTCIC) or by flow cytometry prior and subsequent to incubation.

In murine studies, the highest enrichment of HSC activity yet reported describes combinations of markers, such as those used to isolate Thy-1.11oSca-1+lineage-Mac-1-CD4—c-kit+ cells, from which about one out of every five intravenously injected cells are able to home to bone marrow and engraft. The phenotype for a highly enriched human stem cell fraction is reported as CD34+, Thy-1+ and lin−, but it is to be understood that the present invention is not limited to the expansion of this stem cell population.

C. Cell Culture and Expansion of Isolated Hematopoietic Stem Cells

The expanded population of stem cells is harvested, for example, from a bone marrow sample of a subject or from a culture. Harvesting hematopoietic stem cells is defined as the dislodging or separation of cells. This is accomplished using a number of methods, such as enzymatic, non-enzymatic, centrifugal, electrical, or size-based methods, or preferably, by flushing the cells using culture media (e.g., media in which cells are incubated) or buffered solution. The cells are optionally collected, separated, and further expanded generating even larger populations of HSC and differentiated progeny.

In general, cells useful for the invention can be maintained and expanded in culture medium that is available to and well-known in the art. Such media include, but are not limited to, Dulbecco's Modified Eagle's Medium (DMEM), DMEM F12 Medium, Eagle's Minimum Essential Medium, F-12K Medium, Iscove's Modified Dulbecco's Medium, RPMI-1640 Medium, and serum-free medium for culture and expansion of hematopoietic cells, such as SFEM. Many media are also available as low-glucose formulations, with or without sodium pyruvate.

Also contemplated herein is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements and bovine embryonic fluid. It is understood that sera can be heat-inactivated at 55-65° C. if deemed necessary to inactivate components of the complement cascade.

Additional supplements also can be used advantageously to supply the cells with the necessary trace elements for optimal growth and expansion. Such supplements include insulin, transferrin, sodium selenium and combinations thereof. These components can be included in a salt solution such as, but not limited to, Hanks' Balanced Salt Solution (HBSS), Earle's Salt Solution, antioxidant supplements, MCDB-201 supplements, phosphate buffered saline (PBS), ascorbic acid and ascorbic acid-2-phosphate, as well as additional amino acids. Many cell culture media already contain amino acids; however, some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Hormones also can be advantageously used in the cell cultures of the present invention and include, but are not limited to, D-aldosterone, diethylstilbestrol (DES), dexamethasone, beta-estradiol, hydrocortisone, insulin, prolactin, progesterone, somatostatin/human growth hormone (HGH), thyrotropin, thyroxine, and L-thyronine.

Lipids and lipid carriers also can be used to supplement cell culture media, depending on the type of cell and the fate of the differentiated cell. Such lipids and carriers can include, but are not limited to, cyclodextrin ($\alpha$, $\beta$, $\gamma$), cholesterol, linoleic acid conjugated to albumin, linoleic acid and oleic acid conjugated to albumin, unconjugated linoleic acid, linoleic-oleic-arachidonic acid conjugated to albumin and oleic acid unconjugated and conjugated to albumin, among others.

Also contemplated in the present invention is the use of feeder cell layers. Feeder cells are used to support the growth of fastidious cultured cells, such as stem cells. Feeder cells are normal cells that have been inactivated by $\gamma$-irradiation. In culture, the feeder layer serves as a basal layer for other cells and supplies cellular factors without further growth or division of their own. Examples of feeder layer cells are typically human diploid lung cells, mouse embryonic fibroblasts and Swiss mouse embryonic fibroblasts, but can be any post-mitotic cell that is capable of supplying cellular components and factors that are advantageous in allowing optimal growth, viability and expansion of stem cells. In many cases, feeder cell layers are not necessary to keep stem cells in an undifferentiated, proliferative state, as leukemia inhibitory factor (LIF) has anti-differentiation properties. Therefore, supplementation with LIF can be used to maintain cells in an undifferentiated state.

Cells may be cultured in low-serum or serum-free culture medium. Serum-free medium used to culture cells is described in, for example, U.S. Pat. No. 7,015,037. Many cells have been grown in serum-free or low-serum medium. For example, the medium can be supplemented with one or more growth factors. Commonly used growth factors include, but are not limited to, bone morphogenic protein, basic fibroblast growth factor, platelet-derived growth factor and epidermal growth factor, stem cell factor, thrombopoietin, and Flt3 ligand. See, for example, U.S. Pat. Nos. 7,169,610; 7,109,032; 7,037,721; 6,617,161; 6,617,159; 6,372,210; 6,224,860; 6,037,174; 5,908,782; 5,766,951; 5,397,706; and 4,657,866; all incorporated by reference herein for teaching growing cells in serum-free medium.

Cells in culture can be maintained either in suspension or attached to a solid support, such as extracellular matrix components. Stem cells often require additional factors that encourage their attachment to a solid support, such as type I and type II collagen, chondroitin sulfate, fibronectin, "superfibronectin" and fibronectin-like polymers, gelatin, poly-D and poly-L-lysine, thrombospondin and vitronectin. Hematopoietic stem cells can also be cultured in low attachment flasks such as but not limited to Corning Low attachment plates.

D. Cryopreservation of Cells and Blood

Once established in culture, cells can be used fresh or frozen and stored as frozen stocks, using, for example, DMEM with 40% FCS and 10% DMSO. Other methods for preparing frozen stocks for cultured cells also are available to those skilled in the art.

In addition, the stem cells obtained from harvesting according to method of the present invention described above can be cryopreserved using techniques known in the art for stem cell cryopreservation. Accordingly, using cryopreservation, the stem cells can be maintained such that once it is determined that a subject is in need of stem cell transplantation, the stem cells can be thawed and transplanted back into the subject.

More specifically, an embodiment of the present invention provides for the enhancement of HSCs collected from cord blood or an equivalent neonatal or fetal stem cell source, which may be cryopreserved, for the therapeutic uses of such stem cells upon thawing. Such blood may be collected by several methods known in the art. For example, because umbilical cord blood is a rich source of HSCs, an excellent source for neonatal blood is the umbilical cord and placenta. Prior to cryopreservation, the neonatal blood may be obtained by direct drainage from the cord and/or by needle aspiration from the delivered placenta at the root and at distended veins. See, e.g., U.S. Pat. Nos. 7,160,714; 5,114,672; 5,004,681; U.S. Pat. Pub. No. 2003/0032179. Indeed, umbilical cord blood stem cells have been used to reconstitute hematopoiesis in children with malignant and nonmalignant diseases after treatment with myeloablative doses of chemo-radiotherapy. See, Sirchia and Rebulla (1999). See also, Laughlin (2001) and U.S. Pat. No. 6,852,534. Additionally, it has been reported that stem and progenitor cells in cord blood appear to have a greater proliferative capacity in culture than those in adult bone marrow (Salahuddin et al., 1981; Cappellini et al., 1984).

Alternatively, fetal blood can be taken from the fetal circulation at the placental root with the use of a needle guided by ultrasound, by placentocentesis, or by fetoscopy and cryopreserved. The chorionic villus and amniotic fluid, in addition to cord blood and placenta, are sources of pluripotent fetal stem cells (see, WO 2003/042405).

Various kits and collection devices are known for the collection, processing, and storage of cord blood. See, e.g., U.S. Pat. Nos. 7,147,626; 7,131,958. Collections should be made under sterile conditions, and the blood may be treated with an anticoagulant. Such anticoagulants include citrate-phosphate-dextrose, acid citrate-dextrose, Alsever's solution, DeGowin's solution, Edglugate-Mg, Rous-Turner solution, other glucose mixtures, heparin, or ethyl biscoumacetate.

Various procedures are known in the art or described herein and can be used to enrich collected cord blood for HSCs. These include but are not limited to equilibrium density centrifugation, velocity sedimentation at unit gravity, immune rosetting and immune adherence, counterflow centrifugal elutriation, T-lymphocyte depletion, and fluorescence-activated cell sorting, alone or in combination. See, e.g., U.S. Pat. No. 5,004,681.

Typically, collected blood is prepared for cryogenic storage by addition of cryoprotective agents such as DMSO, glycerol, polyvinylpyrrolidine, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, and inorganic salts. Addition of plasma (e.g., to a concentration of 20%-25%) may augment the protective effect of DMSO.

Collected blood should be cooled at a controlled rate for cryogenic storage. Different cryoprotective agents and different cell types have different optimal cooling rates. Considerations and procedures for the manipulation, cryopreservation, and long-term storage of HSC sources are known in the art. See, e.g., U.S. Pat. Nos. 4,199,022; 3,753,357; 4,559,298; 5,004,681. There are also various devices with associated protocols for the storage of blood (U.S. Pat. Nos. 6,226,997 and 7,179,643).

Considerations in the thawing and reconstitution of HSC sources are also known in the art. The HSC source blood may also be treated to prevent clumping and to remove toxic cryoprotective agents. Further, there are various approaches to determining an engrafting cell dose of HSC transplant units. See, U.S. Pat. No. 6,852,534; Kuchler (1964).

E. Methods of Transplantation and Engraftment

The term "engraftment" is used herein to refer to the ability of hematopoietic stem cells or progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic progenitor cells, or survival of a recipient. In one embodiment, engraftment is determined by measuring white blood cell counts in peripheral blood during a post-transplant period. Alternatively, engraftment can be assessed by measuring recovery of marrow cells in a bone marrow aspirate sample.

The term "xenogeneic" is used herein with reference to a host cell or organism to indicate that the material referred to as "xenogeneic" is derived from another species than that of the host cell or organism.

Engraftment of xenogeneic HSC in immunodeficient animals has traditionally required conditioning prior to administration of the HSC, either sub-lethal irradiation of the recipient animal with high frequency electromagnetic radiation, generally using gamma radiation, or treatment with a radiomimetic drug such as busulfan or nitrogen mustard. Conditioning is believed to reduce numbers of host hematopoietic cells, create appropriate microenvironmental factors for engraftment of xenogeneic HSC, and/or create microenvironmental niches for engraftment of xenogeneic HSC. Standard methods for conditioning are known in the art, such as in Hayakawa et al. (2009).

Generally, a HSCT-conditioning regimen is the global immunosuppression of a recipient. These regimens are used to eradicate disease, reduce the efficacy of the recipient's immune system, reduce the recipient's ability to produce additional self HSCs, and deplete cells within the marrow niche. HSCT conditioning is currently being carried out with drugs (e.g., azathioprine, cyclosporine, cyclophosphamide, etc.), radiation (e.g., myeloablative and non-myeloablative), and biologics (e.g., OKT3, CTLY41g, infliximab, etc.).

Myeloablative radiation has many side effects and wipes out the recipient's cells with one high dose. The primary side effects are necrosis and/or apoptosis of the hematolymphoid system and GI tract. The secondary side effects are weight loss, infection, GVHD, and death. Non-myeloablative radiation is performed using a lower dose, has a limited number of side effects, and does not kill off all of the recipient's cells. The primary side effects are necrosis and/or apoptosis of the hematolymphoid system and lesser GI tract, weight loss, and infection.

The HSC administered are isolated from an original source material to obtain a population of cells enriched in HSCs. The isolated HSCs may or may not be pure. According to embodiments, HSCs are purified by selection for a cell marker, such as CD34. According to embodiments, administered HSCs are a population of cells in which CD34+ cells constitute about 1-100% of total cells, although a population of cells in which CD34+ cells constitute less than 1% of total cells can be used. According to embodiments, administered HSCs are T cell depleted cord blood cells in which CD34+ cells make up about 1-3% of total cells, lineage depleted cord blood cells in which CD34+ cells make up about 50% of total cells, or CD34+ positively selected cells in which CD34+ cells make up about 90% of total cells.

The number of HSCs administered is not considered limiting with regard to generation of a xenogeneic hematopoietic and immune system. A single HSC can generate a hematopoietic and immune system. Thus, the number of administered HSCs is generally in the range of $3 \times 10^3$ to $1 \times 10^6$ CD34+ cells where the recipient is a mouse, although more or fewer can be used. For other species, the number of cells can be adjusted if necessary using only routine experimentation.

F. Assessing Engraftment

Engraftment of xenogeneic HSC can be assessed by any of various methods, such as, but not limited to, flow cytometric analysis of cells in the animals to which the xenogeneic HSC are administered at one or more time points following the administration of HSC. Exemplary methods for isolation of xenogeneic HSC, administration of the xenogeneic HSC to a host organism and methods for assessing engraftment thereof are described herein and in Pearson et al. (2008); Ito et al. (2002); Traggiai et al. (2004); Ishikawa et al. (2005); Shultz et al. (2005); Holyoake et al. (1999).

Engraftment can be assessed by measuring hematopoietic blood cell counts; in particular white blood cell counts. Recovery of normal white blood cell counts is a functional measure of successful engraftment. In a clinical context, this can be accompanied by the measurement of cellularity in the bone marrow through serial bone marrow punctions/biopsies and/or by human leukocyte antigen (HLA) typing of circulating white blood cells. Bone marrow aspirates can also be assessed for donor chimerism as a measure of engraftment.

All blood cell types can be indicative of engraftment, but depending on their half lives, provide a more or less sensitive measure of engraftment. Neutrophils have a very short half life (just hours in the blood), and thus are a very good measure of early engraftment. Platelets also have a short half life, but they are usually the last blood element to recover to pre-transplant levels, which may not make them suitable as a marker of early engraftment. Thus, it is noted herein that cells useful for determining engraftment of hematopoietic progenitor cells are those that recover relatively rapidly following transplantation and have a relatively short half-life (e.g., neutrophils).

Engraftment is successful where xenogeneic HSCs and cells differentiated from the HSCs in the recipient animal are detected at a time when the majority of any administered non-HSC have degenerated. Detection of differentiated HSC cells can be achieved by detection of xenogeneic DNA in the recipient animal or detection of intact xenogeneic HSCs and cells differentiated from the HSCs, for example. Serial transfer of CD34+ cells into a secondary recipient and engraftment of a xenogeneic hematopoietic system is a further test of HSC engraftment in the primary recipient. Engraftment can be detected by flow cytometry as 0.05% or greater xenogeneic CD45+ cells in the blood, spleen or bone marrow at 10-12 weeks after administration of the HSC.

III. TREATMENT OF DISEASES OF THE HEMATOPOIETIC SYSTEM

A. Disease of the Hematopoietic System

Hematopoietic progenitor cells or stem cells can be transplanted to regenerate hematopoietic cells in an individual having a disease of the hematopoietic system. Such diseases can include, but are not limited to, cancers (e.g., leukemia, lymphoma), blood disorders (e.g., inherited anemia, inborn errors of metabolism, aplastic anemia, beta-thalassemia, Blackfan-Diamond syndrome, globoid cell leukodystrophy, sickle cell anemia, severe combined immunodeficiency, X-linked lymphoproliferative syndrome, Wiskott-Aldrich syndrome, Hunter's syndrome, Hurler's syndrome Lesch Nyhan syndrome, osteopetrosis), chemotherapy rescue of the immune system, and other diseases (e.g., autoimmune diseases, diabetes, rheumatoid arthritis, system lupus erythromatosis).

B. Cell Transplantation

Transplantation of hematopoietic cells has become the treatment of choice for a variety of inherited or malignant diseases. While early transplantation procedures utilized the entire bone marrow population, recently, more defined populations, enriched for stem cells (CD34 cells) have been used. In addition to the marrow, such cells could be derived from other sources such as bone marrow stem cells mobilized to the peripheral blood and neonatal umbilical cord blood.

The donor and the recipient can be a single individual or different individuals, for example, autologous or allogeneic transplants, respectively. When allogeneic transplantation is practiced, regimes for reducing implant rejection and/or graft vs. host disease, as well known in the art, should be undertaken. Such regimes are currently practiced in human therapy. The cell populations selected can also be depleted of T lymphocytes, which may be useful in the allogeneic and haploidentical transplants setting for reducing graft-versus-host disease. Alternatively, the donor cells may be xenogeneic.

In another embodiment of the invention, INPROL can be employed in a method for preparing autologous hematopoietic cells for transplantation, as described in U.S. Pat. No. 7,115,267, which is herein incorporated by reference in its entirety. The hematopoietic cells are treated ex vivo with an effective amount of INPROL to inhibit stem cell division and then purged of cancerous cells by administering to the marrow cultures an effective amount of a chemotherapeutic agent or radiation. Chemotherapy agents with specificity for cycling cells are preferred. Marrow thus treated is re-injected into the autologous donor. Optionally, the patient is treated with stem cell stimulatory amounts of INPROL and/or another agent known to stimulate hematopoiesis to improve the hematopoietic reconstitution of the patient. Such a technique allows for effective purging of tumor cells during autologous bone marrow grafts while protecting hematopoietic stem cells. Such protection can be afforded with either ex vivo or in vivo purging protocols. Once successfully transplanted, there is a need for stem cells to rapidly proliferate to regenerate normal bone marrow function. This can be afforded by the use of INPROL at stem cell stimulatory amounts which stimulates cycling of stem cells and enhances recovery of bone marrow function.

C. Methods for Administering Cells

Stem cells can be administered to a subject either locally or systemically. Methods for administering bone marrow transplants to a subject are known in the art. In certain embodiments, bone marrow cells from a healthy patient can be removed, preserved, and then replicated and re-infused should the patient develop an illness which either destroys the bone marrow directly or whose treatment adversely affects the marrow. If the patient is receiving his or her own cells, this is called an autologous transplant; such a transplant has little likelihood of rejection.

Exemplary methods of administering stem cells to a subject, particularly a human subject, include injection or transplantation of the cells into target sites in the subject. The hematopoietic stem cells and/or hematopoietic progenitor cells can be inserted into a delivery device which facilitates introduction, by injection or transplantation, of the cells into the subject. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The stem cells can be inserted into such a delivery device, e.g., a syringe, in different forms. For example, the cells can be suspended in a solution, or alternatively embedded in a support matrix when contained in such a delivery device.

Support matrices in which the stem cells can be incorporated or embedded include matrices that are recipient-compatible and that degrade into products that are not harmful to the recipient. The support matrices can be natural (e.g., collagen, etc.) and/or synthetic biodegradable matrices. Synthetic biodegradable matrices include synthetic polymers such as polyanhydrides, polyorthoesters, and polylactic acid.

As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is known in the art. The solution is preferably sterile and fluid to the extent that easy syringability exists.

Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating stem cells as described herein in a pharmaceutically acceptable carrier or diluent and, as required, other ingredients enumerated above, followed by filtered sterilization.

D. Dosage and Administration

In one aspect, the methods described herein provide a method for enhancing engraftment of hematopoietic stem and/or progenitor cells following a bone marrow transplant in a subject. In one embodiment, the subject can be a mammal. In another embodiment, the mammal can be a human, although the invention is effective with respect to all mammals.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of each active ingredient required to be administered depend on the judgment of the practitioner and are particular to each individual. However, suitable dosage ranges depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

E. Efficacy

The efficacy of a given treatment to enhance hematopoietic cell engraftment can be determined by the skilled artisan. However, a treatment is considered "effective treatment," as the term is used herein, if any one or all of the signs or symptoms of e.g., poor hematopoietic cell engraftment are altered in a beneficial manner, other clinically accepted symptoms are improved, or even ameliorated, e.g., by at least 10% following treatment with a compound as described herein. Efficacy can also be measured by a failure of an individual to worsen as assessed by hospitalization, need for medical interventions (i.e., progression of the disease is halted), or incidence of engraftment failure. Methods of measuring these indicators are known to those of skill in the art and/or are described herein. Treatment includes any treatment of a disease in an individual or an animal (some non-limiting examples include a human, or a mammal) and includes: (1) inhibiting the disease, e.g., preventing engraftment failure; or (2) relieving the disease, e.g., causing regression of symptoms. An effective amount for the treatment of a disease means that amount which, when administered to a mammal in need thereof, is sufficient to result in effective treatment as that term is defined herein, for that disease. Efficacy of an agent can be determined by assessing physical indicators of, for example hematopoietic cell engraftment, such as, e.g., neutrophil production, white blood cell count, hematopoietic cell numbers, presence/absence of anemia, etc. Efficacy can be assessed in animal models of bone marrow transplantation, for example treatment of a rodent following bone marrow transplantation, and any treatment or administration of the compositions or formulations that leads to an increase of at least one symptom of hematopoietic cell engraftment.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Animals—

The Kit$^{W41}$ and the NSG strains were obtained from the Jackson Laboratory (Shultz et al., 2005; Nocka et al., 1990; Reith et al., 1990; Geissler et al., 1981). All mice were housed in accordance with guidelines set forth by the University of Wisconsin Medical School's Animal Care and Use Committee. Mice were housed in ventilated micro-isolator cages on corncob bedding with autoclaved water and irradiated food ad libitum in a high-barrier facility under specific pathogen-free conditions.

Generation of the NSGW Mice—

To generate NSGW mice, Kit$^{W41/W41}$ mice were produced. The male Kit$^{W41/W41}$ mice were crossed with female NSG mice. The F2 progeny were then intercrossed. The F3 progeny were genotyped and selected for the following homozygous status: Prkdc$^{scid}$, Il2rg$^{-/-}$, Kit$^{W41/W41}$.

Genotyping—

To confirm the Kit$^{W41}$ allele, DNA was amplified by PCR using o143 and o144. The amplicon was sequenced using o144. Mice were genotyped for a single G/A nucleotide polymorphism at nucleotide 75,652,562 in the *Mus musculus* Kit gene (NC_000071.6). To confirm the Prkdc$^{SCID}$ allele, DNA was amplified by PCR using o149 and o150. The amplicon was sequenced using o150. Mice were genotyped for a single T/A nucleotide polymorphism at nucleotide 15,839,180 in the *Mus musculus* Prkdc gene (NC_000082.6). The IL2Rγ$^-$ genotyping protocol was previously published (Shultz et al., 2005). To confirm the Tyr allele, DNA was amplified by PCR using o1111 and o1112. The amplicon was sequenced using o1111. Mice were genotyped for a single G/C nucleotide polymorphism at nucleotide 5,241,720 in the *Mus musculus* Tyr gene (NT_039433.8). To confirm the Sripa allele, DNA was amplified by PCR using o1113 and o1114. The amplicon was sequenced using both o1113 and o1114 in separate reactions. Sequences were aligned to the C57BL/6J genome (NT_039207.8). Sequences were analyzed at seven bases between nucleotides 70,488,250 and 70,488,290 for homozygosity and for the NOD specific polymorphisms (FIG. 7). All sequence analysis was performed using DNAS-TAR® SeqMan Pro software (Madison, Wis.).

Oligonucleotides—

Oligonucleotides were synthesized by Integrated DNA Technologies (Table 1, IDT, Coralville, Iowa).

TABLE 1

| Name | Sequence (5' to 3') | SEQ ID NO: |
|---|---|---|
| o17 | GTGGGTAGCCAGCTCTTCAG | 1 |
| o18 | CCTGGAGCTGGACAACAAAT | 2 |
| o19 | GCCAGAGGCCACTTGTGTAG | 3 |
| o143 | AGAGAGGTGGCAAATCAGTGTCCA | 4 |
| o144 | CCCTGGACTTCTCTGCTCTTAGTT | 5 |
| o149 | TAAAGCCGCCCTAAGAGTCA | 6 |
| o150 | CCCTTAGAGTTTTGAGCAGACA | 7 |
| o1111 | ATCCTTCTGTCCAGTGCACCATCT | 8 |
| o1112 | CTCGCTTCTCTGTACAATTTGGGC | 9 |
| o1113 | CCTGCAGGATCCCTTAAGGTTAGT | 10 |
| o1114 | CCCTACTCCTCTGTACCACCTAAT | 11 |

Human Cell Engraftment—

Frozen human CD34+ cord blood cells (CBCs) were obtained from All Cells, LLC. Cells were thawed per the manufacturer's recommendation and incubated overnight in serum free media (StemCell Technologies) supplemented with SCF (100 ng/mL, Peprotech). The next morning, live cells were enumerated using a hemocytometer and trypan blue exclusion. Cells were suspended at $1.25 \times 10^6$/mL in Hank's Balanced Salt Solution (HBSS, Life Technologies Corp.). Each mouse was injected with 200 µL retro-orbitally while experiencing isoflurane anesthesia (Yardeni et al., 2011). Quality control was performed on the overnight CD34+ cell culture by Fluorescent Activated Cell Sorting (FACS) for the percentage of cells expressing CD34.

Human Xenograft Analysis—

Post-injection, every two-weeks over a twelve-week period, a 50 µL blood sample was drawn into heparin coated capillary tubes (Fisher Scientific) from the retro-orbital sinus. Each blood sample was transferred into an EPPEN-DORF® tube containing 150 µL of 2% dextran (Sigma) in PBS and 150 µL of 0.5% Heparin solution (Sigma). Blood was allowed to settle 20 minutes. The translucent upper layer (containing leukocytes) was transferred to 1 mL of red blood cell lysis buffer (RBCLB; 140 mM ammonia chloride, 2 mM Tris, pH 7.6 (Sigma)). After 10 minutes, each tube's volume was increased to 3 mL with cold FACS staining buffer (FSB; HBSS, 2% fetal bovine serum (Hyclone), 10 mM HEPES (Life Technologies, Corp.), 0.1% sodium azide (Sigma)) and the tubes centrifuged to pellet the cells. A second wash with 1 mL of cold FSB was performed, and the tubes were again centrifuged.

For analysis of hemato-lymphoid organs, the femurs, spleen, and, when applicable, thymus were removed. The femurs were flushed with 1 mL of FSB. The spleens were homogenized using an 18-gauge needle, mashed with the blunt end of a 3-mL syringe, and filtered through a 70-micrometer mesh. Both were lysed with RBCLB (as outlined above) and washed.

Samples were stained in 100 µL FSB with the following antibodies: anti-mouse CD45-fluorescein isothiocyanate (FITC; BD 553080), anti-human (α-hu) CD45-allophycocyanin (APC; BD 555485, 340943), α-huCD3-PE (BD 555340, 555333), α-huCD11b-PE (BD 555388), α-huCD15-PE (BD 555402), α-huCD19-PE (BD 349209, 555413), α-huCD33-PE (BD 347787), α-huCD34-PE (BD 348057), α-huCD56-PE (BD 555516), α-huCD66b-PE (BD 561650), α-huGlyA-PE (BD 340947), and α-huIgM-V450 (BD 561286). Viability was assessed using propidium iodide or DAPI (Life Technologies).

FACS was performed on a BD FACSARIA® III equipped with 405-, 488-, 535-, and 633-nm lasers and appropriate filters. When possible, 2000 huCD45+ events were recorded; otherwise, between 50,000 and 100,000 total events were acquired. Positive engraftment was defined using both mouse and human peripheral blood stained with the above antibodies for lineage markers. Cell analysis was performed using FlowJo Version 9.5.2 (TreeStar).

Statistics—

Data was loaded into the statistical software program MStat 5.5 (on the world wide web at mcardle.oncology.wisc.edu/mstat/). A two-sided Wilcoxon rank-sum test was performed to determine the statistical significance between the NSG and NSGW strains.

Gross Pathology—

Organs were harvested from non-xenografted mice, 8- to 10-weeks of age (unless from xenograft experiments).

Histology—

Tissues were fixed in 10% neutral-buffered formalin overnight and transferred to 70% ethanol the following afternoon. Processing, paraffin embedding, and sectioning were performed at the University of Wisconsin Veterinary School Histology Lab. Following embedding, transverse, or sagittal sections (8 μm) were cut through the tissues and every $6^{th}$ slide stained with hematoxylin and eosin.

Immunohistochemistry—

Slides were deparaffinized and antigens were retrieved per the manufacturer's protocol using a DECLOAKING CHAMBER™ Chamber (Biocare Medical, Concord, Calif.). Slides were blocked in 10% horse serum in PBS for 1 hour, and 3% hydrogen peroxide for 5 min, respectively. Samples were then incubated overnight at 4° C. with a primary antibody specific for either α-huCD45 (HI30), α-huCD1a (HI149), α-huCD3 (UCHT1), α-huCD19 (LC1), or isotype IgG1-kappa (eBiosciences), with normal mouse serum in PBS (Vector Labs). A universally biotinylated secondary antibody was applied for 30 min (VECTASTAIN® Universal Secondary), washed in PBS, and incubated in ABC (VECTASTAIN®, Vector Labs) reagent for 30 min. Sections were developed with 3,3'-diaminobenzidine reagent for appropriate times, counterstained with hematoxylin, dehydrated in a series of alcohols, and cover slipped. Slides were analyzed on a Zeiss Axio-Scope A1 with EC Plan-NeoFluar-5×/0.3 and −40×/0.75 objectives. Images were acquired using a Q imaging Micropublisher 3.3RTV color camera and iVision v4.5.0.

Example 2

NSGW Mouse Model for Unconditioned Engraftment of Human Cells

The NSGW Mouse Strain Develops Normally in Utero.

The inventors crossed the NSG mouse strain with mice homozygous for the $Kit^{W41}$ allele. The resultant F2 triple-heterozygous (Prkdc,Il2rg,$Kit^{W41}$) progeny were then intercrossed to produce the expected Mendelian genotypes in a 27:9:9:9:3:3:3:1 ratio.

Three quarters of the resultant progeny from the F3 generation were phenotyped by coat color for their Kit allele status. Homozygous $Kit^{W41/W41}$ mice displayed a Holstein coat with a prominent white stripe down the center of their head (FIG. 1). Due to the NSG strain's albino coat penetrance in 25% of the F3 progeny, Kit status was determined via genotyping by sequencing (GBS) (Byrne et al., 2013). Within this generation, the inventors observed a 1:1 ratio of male to female $NSGW^{41/41}$ mice.

A percentage of mice in subsequent intercrosses continued to exhibit an albino coat. The lack of pigmentation made phenotyping for the homozygous NSGW mice difficult, forcing GBS, which the inventors sought to eliminate the need for. The inventors suspected a SNP in the Tyrosinase (Tyr) allele to be the contributing factor. The inventors intercrossed and selected for mice genotyping homozygous wild type or G/G for the dominant pigmented Tyr allele. The inventors did not observe a single albino animal in successive generational intercrosses.

The Non-Irradiated NSGW Strain Exhibits Higher Levels of Human Chimerism in the Blood when Compared to the NSG Strain.

To determine if the $Kit^{W41}$ allele would increase human chimerism in unconditioned 8- to 10-week old mice, the inventors injected, via the retro-orbital sinus, $2.5 \times 10^5$ human CD34+ CBCs into the two strains. Every other week, peripheral blood was drawn and analyzed via FACS for the presence of human and mouse blood cell surface proteins. In two independent experiments (N=3, N=5 each group, FIGS. 2 and 8A), and at each independent time point, the NSGW strain engrafted at higher levels than the NSG strain. Surprisingly, at two-weeks post engraftment, both strains exhibited significant levels of circulating human cells in the peripheral blood. However, when the peripheral blood was analyzed at four-weeks, each strain exhibited a ~6-to ~16-fold increase in circulating cells staining positive for the Human Leukocyte Common Antigen (huCD45), with the NSGW strain being the later. Both unconditioned strains continued to exhibit increased engraftment and proliferation up to week ten. At the ten-week time-point, the level of circulating human cells plateaued. It is speculation, that this leveling may be attributed to cells that are short-term, rather than long-term engraftable HSCs, ending their residence in the peripheral blood. However, at the twelve-week time-point the average percent human chimerism observed in the NSGW strain (61%±2%) measured 9-fold higher when compared to the parental control NSG strain (8.3%±1.2%, FIGS. 2 and 8).

Figure 2:
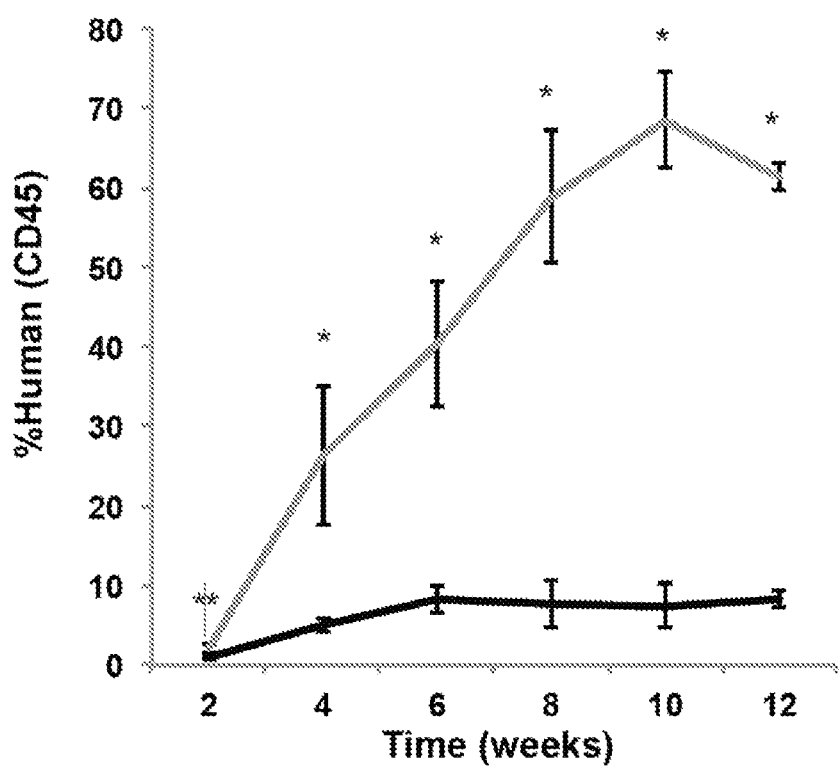
FIG. 2—Bi-weekly monitoring of the human chimerism in the peripheral blood of NSG (black) and of NSGW (grey) strains in the absence of an irradiation conditioning regime. Error is represented by standard deviation (stdev, N=5, **p<0.05, *p<0.01).
Figure 8:
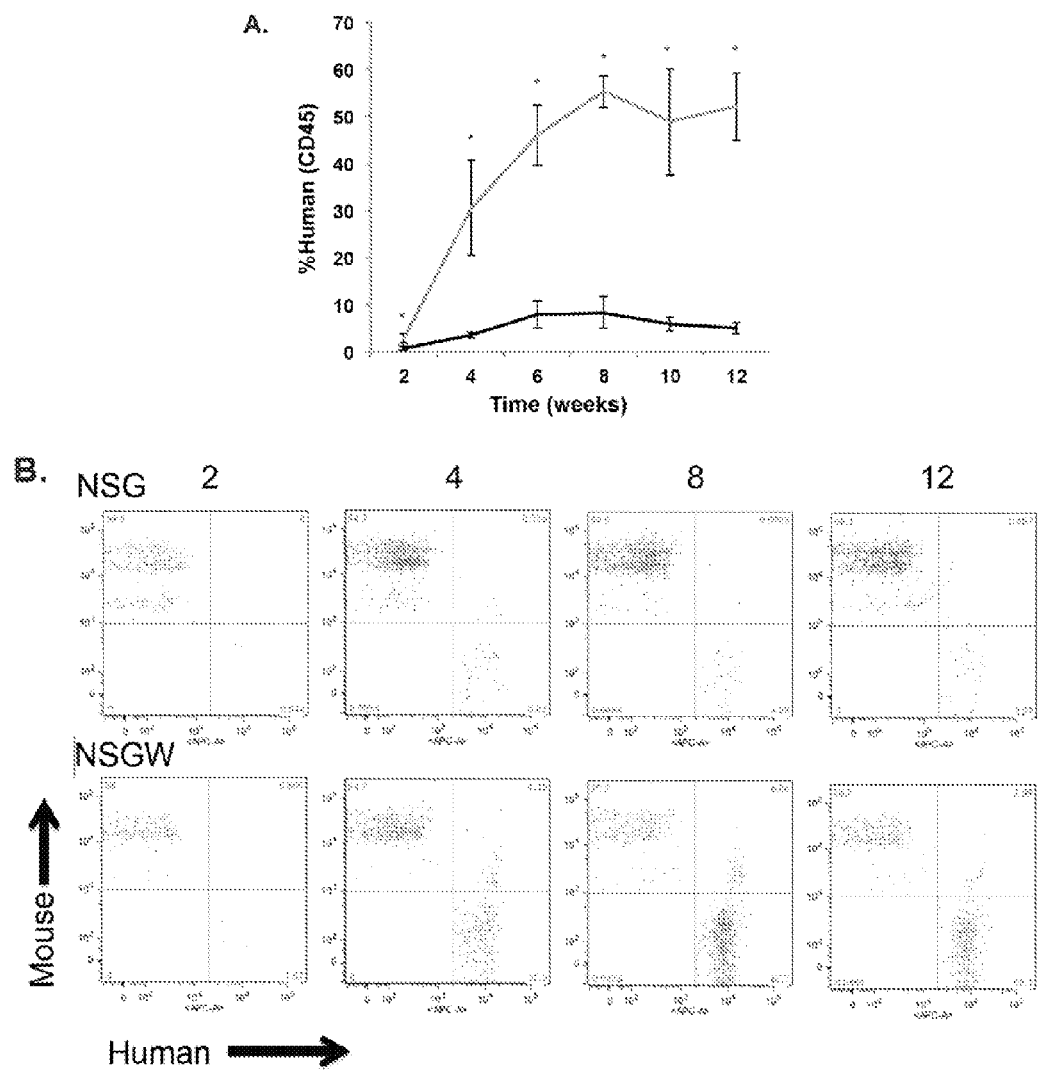
FIGS. 8A-B—(A) Bi-weekly monitoring of the human chimerism in the peripheral blood of NSG (black) and of NSGW (grey) strains in the absence of an irradiation-conditioning regimen. Error is represented by standard deviation (stdev, N=3, *p<0.01). (B) Representative panels of peripheral blood monitoring of NSG and NSGW strains in the absence of an irradiation-conditioning regime. "Mouse" is the expression of mouse CD45 receptor and "Human" is the expression of human CD45 receptor. Values are time in weeks.
Figure 9:
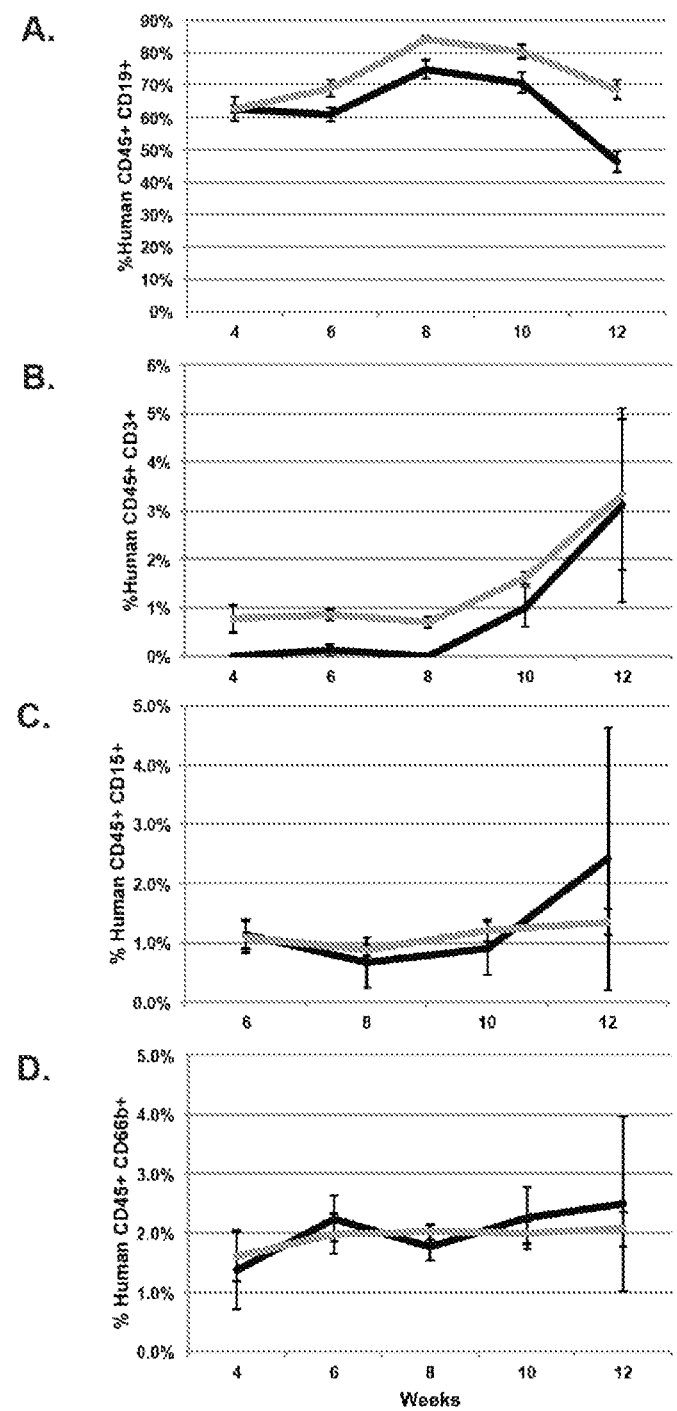
FIGS. 9A-D—Bi-weekly monitoring of the human myelo-lymphoid lineages in the peripheral blood of NSG (black) and of NSGW (grey) strains in the absence of an irradiation-conditioning regimen. The values are represented as the percentage of CD45+ cells staining positive for (A) CD19, (B) CD3, (C) CD15, and (D) CD66b. Error is represented by stdev (N=5).
Figure 10:
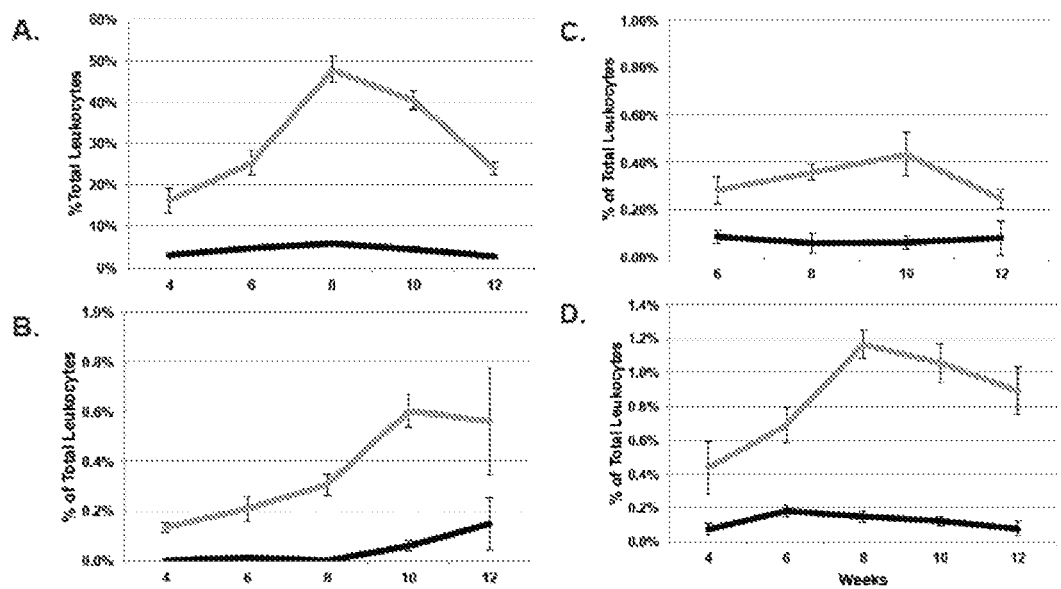
FIGS. 10A-D—Bi-weekly monitoring of the human myelo-lymphoid lineages in the peripheral blood of NSG (black) and of NSGW (grey) strains in the absence of an irradiation-conditioning regime. The values are represented as the percentage of leukocytes staining positive for (A) CD19, (B) CD3, (C) CD15, and (D) CD66b within the total white blood cell population. Error is represented by stdev (N=5).
Figure 11:
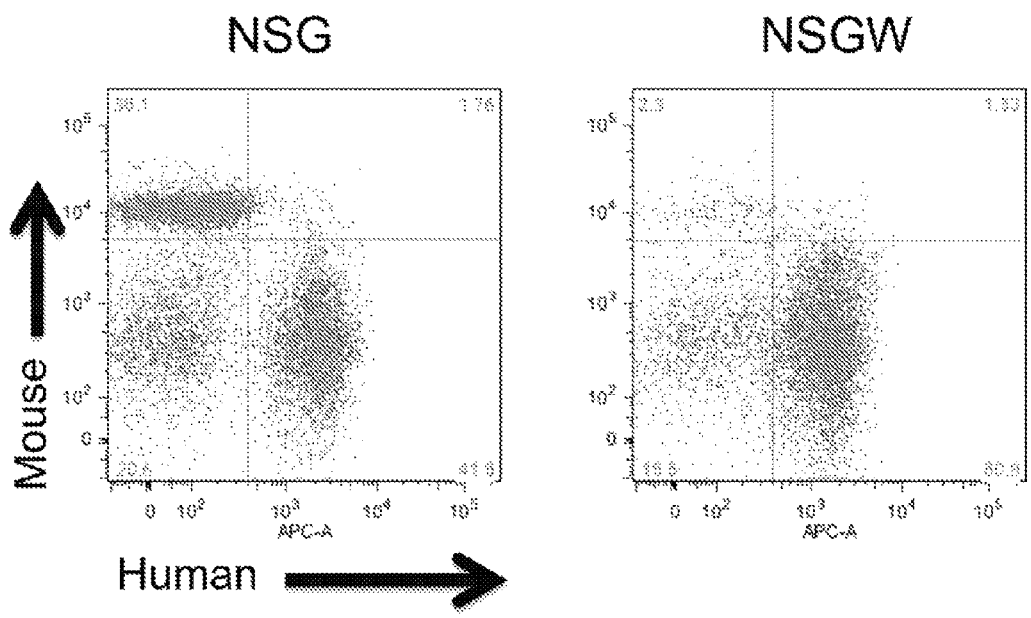
FIG. 11—Representative panels of bone marrow from non-irradiated NSG and NSGW strains 12-weeks post engraftment. "Mouse" is the expression of mouse CD45 receptor and "Human" is the expression of human CD45 receptor.

Analysis of the huCD45+ mouse (ms) CD45− population in both the NSG and NSGW strains indicated similar percentages of committed leukocytes being produced at 12-weeks post engraftment (Table 2). However, based on the statistically significant increase in the number of human cells in the NSGW strain, by default the human cell numbers must be greater in this strain (FIGS. 2, 8, and 9). Of the committed lympho-myelyoid cells, both T-cells (CD3+), and myeloid (CD11b+, CD15+, CD66b+) cells were produced to similar percentages (Table 2; FIGS. 10A-D). However, the B-cell compartment displayed a significant difference in the percentages of cells between the two strains (Table 2). The NSG strain exhibited 46.4%±3.2% of the huCD45+ msCD45− population to be CD19+, while the NSGW strain was observed at a value of 68.4%±2.9% (p<0.01). Further analysis of the CD19+ population's engraftment kinetics amongst total leukocytes over the 12-week period indicated a bias toward the production of human B cells in both strains over their lymphoid/myeloid contemporaries (FIGS. 9 and 10).

TABLE 2

Observed percentages of human cells in the peripheral
blood of mice engrafted at 12-weeks

|  | NSG | NSGW |
|---|---|---|
| CD3+ (T cell) | 3.1% ± 2.0% | 3.3% ± 1.5% |
| CD19+ (B cell) | 46.4% ± 3.2% | 68.4% ± 2.9%* |
| CD11b+ (myeloid) | 3.4% ± 1.4% | 2.5% ± 0.5% |
| CD15+ (Neut, Eos, Mono) | 2.4% ± 2.2% | 1.4% ± 0.2% |
| CD66b+ (Gran) | 2.5% ± 1.5% | 2.1% ± 0.3% |

Error is represented by standard deviation (stdev, N = 5,
*p < 0.01).

Chimerism in the Marrow.

Analysis of the bone marrow compartment at 12-weeks post-engraftment indicated that both NSG and NSGW strains are capable of accepting human cells without irradiation. This has been recently reported for the NSG strain (Bueno et al., 2010; Brehm et al., 2012). Surprisingly the inventors observed the highest level of chimerism in the marrow of the NSGW strain at 97%±0.4% (FIG. 3A). In comparison, the human chimerism observed in the NSG strain was measured at 30%±9% (p<0.01). The enumerated value for the NSG strain is surprising given the fact that this observation is being made without irradiation. This illustrates the native engraftment efficiency of the parental NSG model, and its contribution to the engraftment level observed in the derived NSGW strain. Resident lymphoid cells in the marrow were also assessed. Both the resident marrow T cells (CD3+) and B cells (CD19+) were observed at similar levels in both strains (Table 3).

TABLE 3

Observed percentages of human cells in the
marrow of mice engrafted at 12-weeks

|  | NSG | NSGW |
|---|---|---|
| CD3+ (T cell) | 3.5% ± 0.5% | 5.4% ± 1.0% |
| CD19+ (B cell) | 89.0% ± 1.0% | 86.0% ± 2.0% |
| CD19+IgM+ (B cell) | 0.5% ± 0.1% | 0.3% ± 0.1% |

Error is represented by stdev (N = 5).

Further analysis of the huCD45+ msCD45− population in the marrow indicated that the NSGW mice attain increased percentages of both hematopoietic progenitor (CD34+) and myeloid cells (CD33+) when compared to the NSG strain (FIGS. 3B-3C). These cell populations were enumerated at 6.4%±1.7% and 6.0%±0.8%, respectively, for the NSG strain, and 18.6%±2.5% and 9.6%±1.8% for the NSGW strain (p<0.01). These data indicate the engraftment and proliferation of the CD34+ hematopoietic cell populations in both stains. However, the more permissive NSGW strain engrafts and expands better in non-irradiation conditions than the NSG strain. In support of this idea is the expansion and increase in the myeloid population, also indicating either a greater number of engrafted progenitors, or a favorable environment for myeloid proliferation.

To assess the possibility of human erythroid cells populating the marrow, the inventors assessed the huCD45− msCD45− population for the presence of Glycophorin A (GpA). Interestingly, a GpA population in the NSG strain was barely detectable (0.12%±0.04%), while in the NSGW strain the GpA population was abundant (26.4%±10.4%, FIG. 3D). This indicates that the engrafted human CD34+ cells also contribute to the erythroid progenitor and further mature red blood cells in the NSGW model.

Chimerism in the Spleen.

Figure 4:
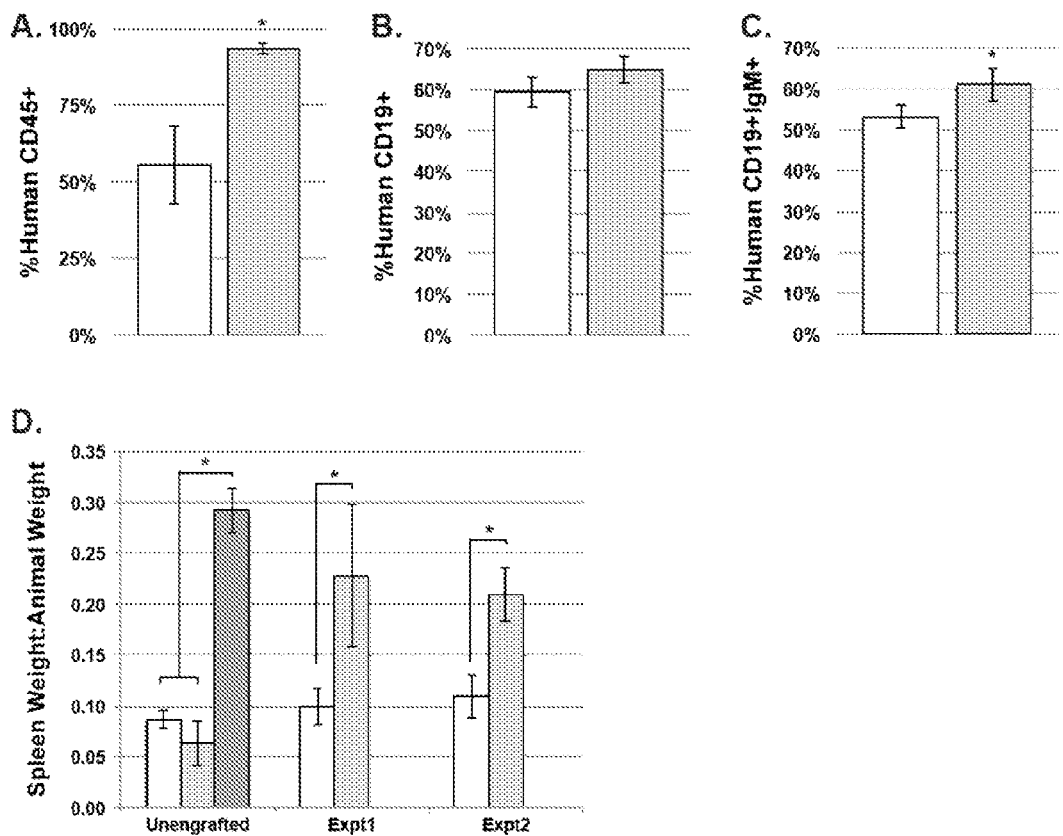
FIGS. 4A-D—Human chimerism, lineage development, and gross pathology observed in the spleen of non-irradiated NSG (white) and NSGW (grey) mice at 12-weeks post engraftment. (A) The percentage of human CD45+ splenocytes. The percentage of human (B) CD19+ cells and (C) CD19+IgM+ cells observed in the human CD45+ fraction. (D) A ratio of the total weight of the spleen to the total weight of the mouse in basal state (unengrafted, N=4) and two xenograft experiments (Expt1, N=5 and Expt2, N=3 C57BL/6J=dark grey). Error is represented by stdev (N=5, *p<0.01).
Figure 5:
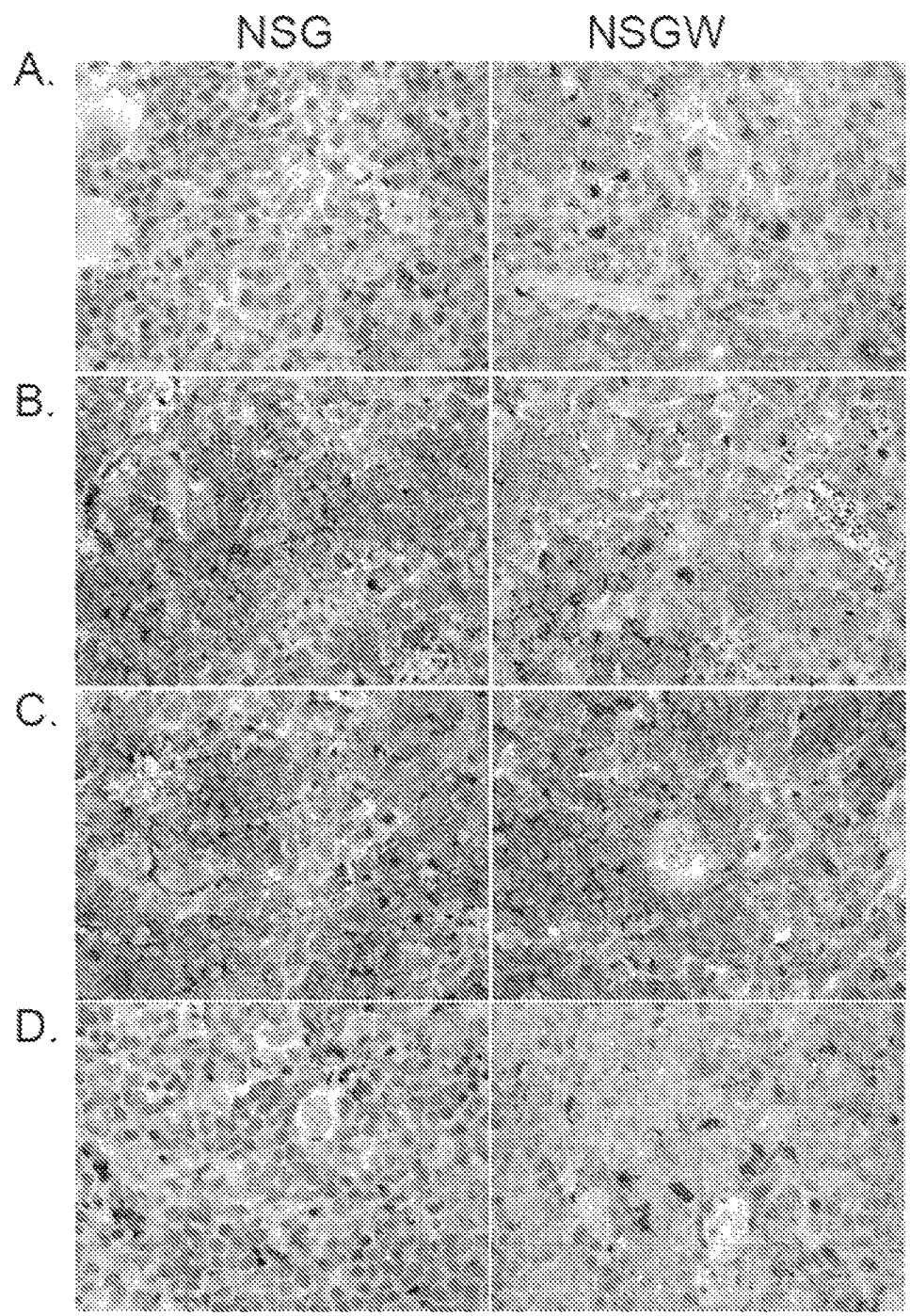
FIGS. 5A-D—Histology of human chimerism and lineage development observed in the spleen of non-irradiated NSG and NSGW mice at 12-weeks post engraftment. Photomicrographs of representative samples are the median from each cohort. Spleens stained with (A) anti-human CD45 (splenocyte), (B) anti-human CD19 (B-cell), (C) anti-human CD11b (myeloid), and (D) anti-human CD1a (dendritic) and counterstained with hematoxylin.

Analysis of the spleens by FACS supported the idea that both strains are receptive to xenografts without irradiation. Further, the environments of both strains allow for homing and both display development of differentiated hematopoietic progeny. The splenocytes of the NSGW strain were observed at 12-weeks post engraftment to be 94%±2% for huCD45+ indicating a highly humanized spleen (FIG. 4A). The splenocyte population for the NSG strain was also found to be surprisingly high measuring at 55%±13%. To obtain further confirmation of our observations, the inventors performed histology on tissue sections of spleens from xenografted mice. In agreement with our FACS data, the αhuCD45 staining of the tissue sections from the NSG strain did not produce as robust of staining when compared to the NSGW sections (FIG. 5A). This is in support of the NSGW strain being a better surrogate model for studying human hemato/myelo/lymphoid development without conditioning.

Further analysis of the spleen indicated comparable percentages of differentiated hematopoietic progeny between the two strains. The inventors' analysis of the human cell fraction indicated resident T-cells (CD3+) at 3.6%±1.5% and 3.0%±1.5% in the NSG and NSGW strains, respectively (Table 4). The inventors further assessed the natural killer T-cells (CD56low/+) in both strains to be similar (0.8%±0.3% and 1%±0.3%) for both NSG and NSGW strains, respectively (Table 4).

TABLE 4

Observed percentages of T cells in the
spleens of mice engrafted at 12-weeks

|  | NSG | NSGW |
|---|---|---|
| CD3+ (T cell) | 3.6% ± 1.5% | 3.0% ± 1.5% |
| CD56$^{low}$/+ (NKT cell) | 0.8% ± 0.3% | 1.0% ± 0.3% |

Error is represented by stdev (N = 5).

In the spleens, the observed percentages of CD19+ splenocytes is similar in both strains. In the NSG strain, the inventors observed 60%±4% of the CD45+ cells to be CD19+. Although slightly higher than in the NSG, the same population observed in the NSGW was 65%±3% (FIG. 4B). Comparable histological staining of spleen sections is in support of these data (FIG. 5B).

Next, the inventors evaluated B-cell maturation by assessing splenocyte status of CD19+IgM+. The inventors' analysis of the transitional CD19+ population signified a normal B-cell maturation repertoire occurred in both strains of mice. The inventors observed 53%±3% of the huCD45+CD19+ cells to stain positively for IgM in the NSG strain (FIG. 4C). For the NSGW strain the observation of the same population of cells was 61%±4% (FIG. 4C, p=0.013).

Increased Human Chimerism in the NSGW Strain by Histopathology.

Figure 12:
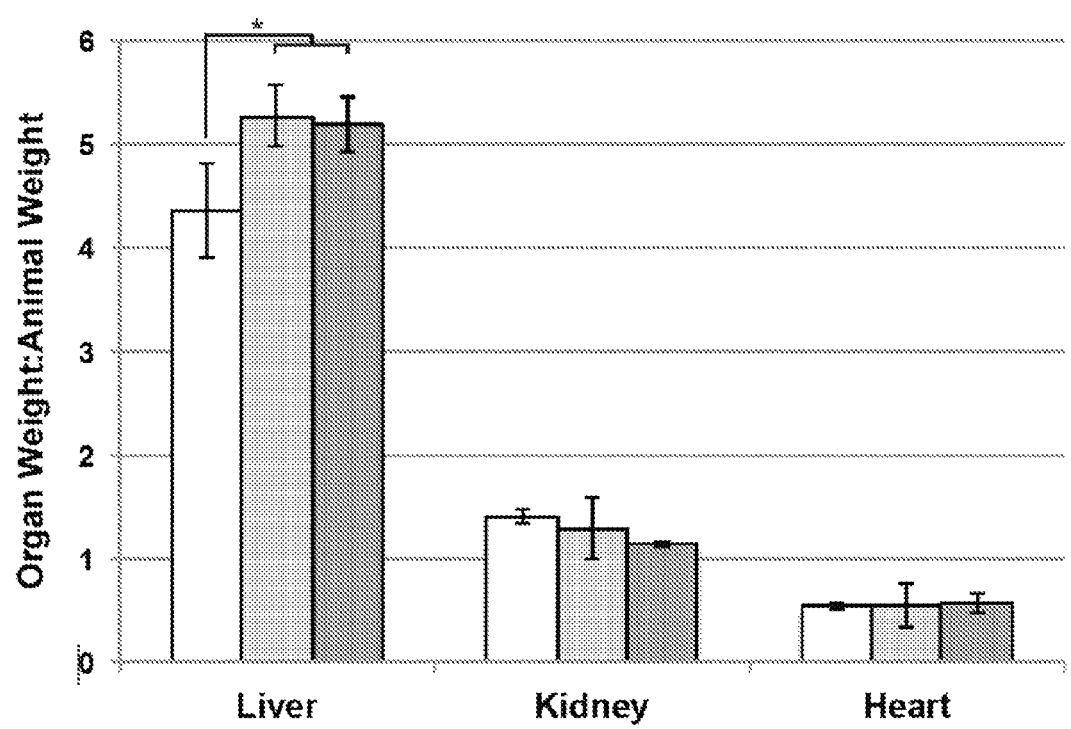
FIG. 12—Gross pathology of the liver, the kidney, and the heart in nonirradiated, unengrafted NSG (white), NSGW (grey), and C57BL/6J (dark grey) mice. A ratio of the total weight of the organ to the total weight of the mouse is illustrated. The error is represented by stdev (N=4, *p<0.05).

The inventors performed gross pathology on a limited number of internal organs (FIGS. 4D and 12). During the analysis two observations pertaining to the organs of the NSGW strain were made. First, unengrafted animals, 8-weeks of age, possess a very thin thymic membrane. The inventors found this structure to be similarly found in the NSG strain. However, the thymic structure of the NSG strain was more defined than that of the NSGW strain.

Figure 6:
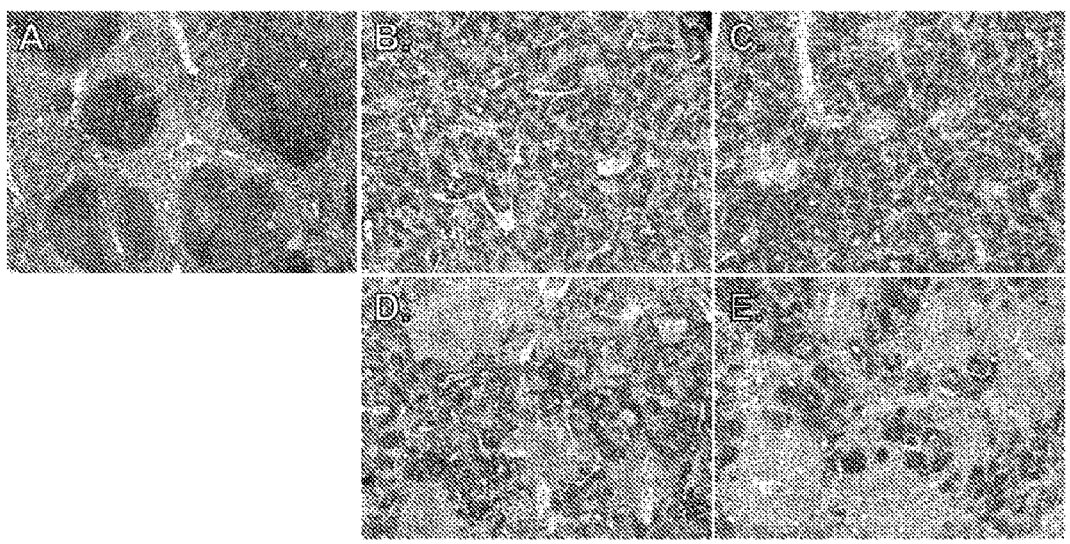
FIGS. 6A-E—Immunocompetent, immunocompromised, and xenografted spleen pathology. Photomicrographs of hematoxylin and eosin stained spleens from non-irradiated, non-engrafted (A) C57BL/6J, (B) NSG, and (C) NSGW; and non-irradiated (D) NSG and (E) NSGW mice at 12-weeks post engraftment.

Spleens from NSGW and NSG mice were on average 6-times smaller compared to those of immunocompetent C57BL/6J mice. Calculating a ratio (weight of the spleen/total body weight of the animal), the inventors made the following observations: NSGW 0.063±0.019, NSG 0.088±0.010, C57BL/6J 0.29±0.02 (FIG. 4D, N=4, p<0.01). Our histological analysis indicated that unlike the spleens of the immunocompetent C57Bl/6J strain, the spleens of unengrafted NSG and NSGW strains lacked the white lymphocyte pulp (FIG. 6). The lack of the white pulp can be attributed to the difference in spleen masses between strains and correlate with strain immunocompetence. Other than lacking white pulp, the spleen architecture appeared normal (i.e. trabeculae, arterioles, and sinuses), indicating a potentially supportive role in both strains once engrafted with HSCs.

The inventors performed similar pathology on all animals from xenograft experiments. Strikingly spleen sizes in the engrafted NSGW doubled (0.23±0.07 and 0.21±0.02) when compared to the NSG controls (0.097±0.021 and 0.11±0.02, FIG. 4D). Further xenografted NSGW spleens almost triple in size compared to their unengrafted NSGW counterparts (FIG. 4D). A comparison of weight ratios between spleens from xenografted NSGW and immunocompetent C57BL/6J strains indicates a shift of the NSGW mice to immunocompetence. Our histological analysis of the NSGW spleens indicated the presence of white pulp (FIG. 6). The inventors conclude that the size differences between the C57BL/6J, NSG and NSGW strains are due to immune-status of the particular strains. Interestingly, on average unengrafted NSGW spleens are smaller than spleens of the NSG strain. This is most likely attributed to the $Kit^{W41}$ mutation.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,753,357
U.S. Pat. No. 4,559,298
U.S. Pat. No. 4,657,866
U.S. Pat. No. 5,004,681
U.S. Pat. No. 5,114,672
U.S. Pat. No. 5,397,706
U.S. Pat. No. 5,677,136
U.S. Pat. No. 5,766,951
U.S. Pat. No. 5,908,782
U.S. Pat. No. 6,037,174
U.S. Pat. No. 6,224,860
U.S. Pat. No. 6,226,997
U.S. Pat. No. 6,372,210
U.S. Pat. No. 6,617,159
U.S. Pat. No. 6,617,161
U.S. Pat. No. 6,852,534
U.S. Pat. No. 7,015,037
U.S. Pat. No. 7,037,721
U.S. Pat. No. 7,109,032
U.S. Pat. No. 7,115,267
U.S. Pat. No. 7,160,714
U.S. Pat. No. 7,169,610
U.S. Pat. No. 7,179,643
U.S. Pat. Pub. No. 2003/0032179
U.S. Pat. Pub. No. 2006/0040389
WO 2003/042405
Baker, Adult cells reprogrammed to pluripotency, without tumors, *Nature Rep. Stem Cells*, Dec. 6, 2007.
Bosma et al., The mouse mutation severe combined immunodeficiency (SCID) is on chromosome 16, *Immunogenetics*, 29:54-56, 1989.
Brehm et al., Engraftment of human HSCs in nonirradiated newborn NOD-scid IL2rgamma null mice is enhanced by transgenic expression of membrane-bound human SCF. *Blood*, 119(12):2778-2788, 2012.
Bueno et al., Intra-bone marrow transplantation of human CD34(+) cells into NOD/LtSz-scid IL-2rgamma(null) mice permits multilineage engraftment without previous irradiation. *Cytotherapy*, 12(1):45-49, 2010.
Byrne et al., Genome wide allele frequency fingerprints (GWAFFs) of populations via genotyping by sequencing. *PLoS One*, 8(3):e57438, 2013.
Capecchi, Altering the genome by homologous recombination, *Science*, 244:1288-1292, 1989.
Cappellini et al., Long-term haemopoiesis in human fetal liver cell cultures, *Brit. J. Haematol.*, 57:61-70, 1984.
Doulatov et al., Hematopoiesis: a human perspective. *Cell Stem Cell*, 10(2):120-136, 2012.
Geissler et al., Analysis of pleiotropism at the dominant white-spotting (W) locus of the house mouse: a description of ten new W alleles. *Genetics*, 97(2):337-361, 1981.
*Handbook of Stem Cells*. Lanza, R. P. et al. (Eds.) Elsevier Academic Press Bulington, M A, 2004.
Hayakawa et al., Busulfan produces efficient human cell engraftment in NOD/LtSz-scid IL2Rγ null mice, *Stem Cells*, 27(1):175-182, 2009.
Holyoake et al., Functional differences between transplantable human hematopoietic stem cells from fetal liver, cord blood, and adult marrow, *Exp. Hematol.*, 27(9):1418-27, 1999.
*Inbred Strains in Biomedical Research*, M. F. W. Festing, The Macmillan Press, London and Basingstoke, 1979.
Ishikawa et al., Development of functional human blood and immune systems in NOD/SCID/IL2 receptor {gamma} chain(null) mice, *Blood*, 106:1565-1573, 2005.
Ito et al., NOD/SCID/gamma(c)(null) mouse: an excellent recipient mouse model for engraftment of human cells, *Blood*, 100:3175-3182, 2002.
Kuchler, In: Biochem. Methods of Cell Culture and Virology, Dowden, Hutchinson & Ross, Strodsburg, Pa., p 18-19, 1964.
Laughlin, Umbilical cord blood for allogeneic transplantation in children and adults, *Bone Marrow Transplant*, 27:1-6 2001.
Marshak et al., Stem Cell Biology, Cold Spring Harbor, New York: Cold Spring Harbor Laboratory Press, 2001.
McDermott et al., Comparison of human cord blood engraftment between immunocompromised mouse strains. *Blood*, 116(2):193-200, 2010.
Nocka et al., Molecular bases of dominant negative and loss of function mutations at the murine c-kit/white spotting locus: W37, Wv, W41 and W. *The EMBO Journal*, 9(6):1805-1813, 1990.

Ohbo et al., Modulation of hematopoiesis in mice with a truncated mutant of the interleukin-2 receptor gamma chain. *Blood,* 87(3):956-967, 1996.

Pearson et al., Creation of "Humanized" Mice to Study Human Immunity, *Curr. Protoc. Immunol.,* 81:15.21.1-15.21.21, 2008.

Reith et al., W mutant mice with mild or severe developmental defects contain distinct point mutations in the kinase domain of the c-kit receptor. *Genes & Development,* 4(3):390-400, 1990.

Rongvaux et al., Human hemato-lymphoid system mice: current use and future potential for medicine. *Annual Review of Immunology,* 31:635-674, 2013.

Salahuddin et al., Long-term suspension cultures of human cord blood myeloid cells, *Blood,* 58:931-938, 1981.

Shultz et al., Human lymphoid and myeloid cell development in NOD/LtSz-scid IL2R gamma null mice engrafted with mobilized human hemopoietic stem cells. *Journal of Immunology,* 174(10):6477-6489, 2005.

Sirchia and Rebulla, Placental/umbilical cord blood transplantation, *Haematologica,* 84:738-747, 1999.

Thomson et al., Embryonic stem cell lines derived from human blastocysts, *Science,* 282:1145-47, 1998.

Traggiai et al., Development of a Human Adaptive Immune System in Cord Blood Cell-Transplanted Mice, *Science,* 304:104-107, 2004.

Vogel and Holden, Field Leaps Forward With New Stem Cell Advances, *Science,* 318:1224-1225, 2007.

Willinger et al., Improving human hemato-lymphoid-system mice by cytokine knock-in gene replacement. *Trends in Immunology,* 32(7):321-327, 2011.

Yarden and Ullrich, Growth factor receptor tyrosine kinases. *Annual Review of Biochemistry,* 57:443-478, 1998.

Yardeni et al., Retro-orbital injections in mice. *Lab Animal,* 40(5):155-160, 2011.

What is claimed is:

1. A mouse whose genome comprises: (i) a homozygous non-obese diabetic (NOD) polymorphism of a Sirpa gene; (ii) a homozygous scid mutation of a Prkdc gene, wherein the homozygous scid mutation of the Prkdc gene is a T to A transversion at codon 4095, wherein the T to A transversion at codon 4095 creates a premature stop codon; (iii) a homozygous disruption of a Il2rγ gene, wherein the disruption causes the ablation of Il2rγ protein expression; and (iv) a homozygous W41 mutation of a Kit gene, wherein the homozygous W41 mutation of the Kit gene is a V to M substitution at residue 831 of the c-Kit gene, wherein said mouse tolerates xenogeneic hematopoietic stem cell transplantation without the need for irradiation prior to said transplantation.

2. The mouse of claim 1, further comprising a homozygous genotype at nucleotide 291 of a Tyrosinase gene, wherein the homozygous genotype is a G at nucleotide 291 of the Tyrosinase gene.

3. The mouse of claim 2, wherein the mouse is not albino.

4. The mouse of claim 1, wherein the mouse is immunodeficient.

5. The mouse of claim 1, wherein the mouse has a C57BL/6J genetic background.

6. The mouse of claim 1, wherein the homozygous disruption of the Il2rγ gene is further defined as a homozygous replacement of part of exon 3 and all of exons 4-8 of the Il2rγ gene with a neomycin resistance cassette.

7. The mouse of claim 1, further comprising xenogeneic hematopoietic stem cells.

8. The mouse of claim 7, wherein the xenogeneic hematopoietic stem cells are human hematopoietic stem cells.

9. The mouse of claim 8, wherein the human hematopoietic stem cells are CD34+ umbilical cord blood-derived cells.

10. A method of xenogeneic hematopoietic cell engraftment in a mouse according to claim 1, comprising administering xenogeneic hematopoietic cells to the mouse absence of irradiation of the mouse.

11. The method of claim 10, wherein the mouse is not irradiated prior to administering the xenogeneic stem cells.

12. A method of claim 10, wherein the xenogeneic hematopoietic cells are xenogeneic hematopoietic stem cells.

13. The method of claim 12, wherein the xenogeneic hematopoietic stem cells are human hematopoietic stem cells.

14. The method of claim 13, wherein the human hematopoietic stem cells are CD34+ umbilical cord blood-derived cells.

15. The method of claim 13, wherein the engraftment level of human CD45+ cells in the bone marrow of the mouse is 80% or more.

16. The method of claim 15, wherein the engraftment level of human CD45+ cells in the bone marrow of the mouse is 90% or more.

17. The method of claim 13, wherein the engraftment level of human CD45+ cells in the spleen of the mouse is 80% or more.

* * * * *

```
                           SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
gtgggtagcc agctcttcag                                                      20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
cctggagctg gacaacaaat                                                      20

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
gccagaggcc acttgtgtag                                                      20

<210> SEQ ID NO 4
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 4
agagaggtgg caaatcagtg tcca                                                 24

<210> SEQ ID NO 5
<211> LENGTH: 24
<212> TYPE: DNA
<213> ORGANISM: Artificial Sequence
<220> FEATURE:
```

<223> OTHER INFORMATION: Synthetic polynucleotide

<400> SEQUENCE: 5
ccctggactt ctctgctctt agtt                                               24

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
taaagccgcc ctaagagtca                                                    20

<210> SEQ ID NO 7
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 7
cccttagagt tttgagcaga ca                                                 22

<210> SEQ ID NO 8
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 8
atccttctgt ccagtgcacc atct                                               24

<210> SEQ ID NO 9
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 9
ctcgcttctc tgtacaattt gggc                                               24

<210> SEQ ID NO 10
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 10
cctgcaggat cccttaaggt tagt                                               24

<210> SEQ ID NO 11
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 11
ccctactcct ctgtaccacc taat                                               24

```
<210> SEQ ID NO 12
<211> LENGTH: 43
<212> TYPE: DNA
<213> ORGANISM: Mus musculus

<400> SEQUENCE: 12
atctttcttc ccaggagcca cggggaagga actgaaggtg act              43

<210> SEQ ID NO 13
<211> LENGTH: 43
<212> TYPE: DNA
<213> ORGANISM: Mus musculus

<400> SEQUENCE: 13
atttttcttt ccaggagcca cgaggacaga agtgaaggtg att              43
```